United States Patent
Fukuzaki et al.

(10) Patent No.: US 12,213,377 B2
(45) Date of Patent: Jan. 28, 2025

(54) ORGANIC THIN FILM TRANSISTOR, ORGANIC SEMICONDUCTOR FILM, COMPOUND, ORGANIC THIN FILM TRANSISTOR-FORMING COMPOSITION, AND METHOD OF MANUFACTURING ORGANIC THIN FILM TRANSISTOR

(71) Applicants: FUJIFILM Corporation, Tokyo (JP);
The University of Tokyo, Tokyo (JP)

(72) Inventors: Eiji Fukuzaki, Kanagawa (JP); Tetsuya Watanabe, Kanagawa (JP); Yoshihisa Usami, Kanagawa (JP); Yukio Tani, Kanagawa (JP); Toshihiro Okamoto, Tokyo (JP); Junichi Takeya, Tokyo (JP)

(73) Assignees: FUJIFILM Corporation, Tokyo (JP);
The University of Tokyo, Tokyo (JP)

( * ) Notice: Subject to any disclaimer, the term of this patent is extended or adjusted under 35 U.S.C. 154(b) by 771 days.

(21) Appl. No.: 17/382,961

(22) Filed: Jul. 22, 2021

(65) Prior Publication Data
US 2021/0351363 A1    Nov. 11, 2021

Related U.S. Application Data

(60) Division of application No. 16/224,903, filed on Dec. 19, 2018, now Pat. No. 11,107,996, which is a
(Continued)

(30) Foreign Application Priority Data

Jun. 27, 2016 (JP) .................................. 2016-126449
Jun. 23, 2017 (JP) .................................. 2017-122786

(51) Int. Cl.
*H10K 85/60* (2023.01)
*C07D 471/06* (2006.01)
(Continued)

(52) U.S. Cl.
CPC ....... *H10K 85/6572* (2023.02); *C07D 471/06* (2013.01); *C07D 471/22* (2013.01);
(Continued)

(58) Field of Classification Search
CPC .. C07D 471/22; C07D 471/06; C07D 491/22; H01L 51/0072; H01L 51/0053;
(Continued)

(56) References Cited

U.S. PATENT DOCUMENTS 7,723,521 B2   5/2010   Bienewald et al.
8,022,214 B2 *  9/2011   Facchetti ............. H10K 85/621
                                                            546/37
(Continued)

FOREIGN PATENT DOCUMENTS

CN    101952988 A    1/2011
CN    102933581 A    2/2013
(Continued)

OTHER PUBLICATIONS

An Office Action mailed by China National Intellectual Property Administration on Feb. 21, 2022, which corresponds to Chinese Patent Application No. 201780038047.9 and is related to U.S. Appl. No. 17/382,961; with English language translation.
(Continued)

*Primary Examiner* — Ling Siu Choi
*Assistant Examiner* — Ronald Grinsted
(74) *Attorney, Agent, or Firm* — Studebaker & Brackett PC

(57) ABSTRACT

Provided are an organic thin film transistor, an organic semiconductor film, a compound, an organic thin film transistor-forming composition, and a method of manufacturing the organic thin film transistor. The organic thin film transistor includes the organic semiconductor film. The organic semiconductor film includes a compound represented by a
(Continued)

specific formula. The organic semiconductor film, the compound, and the organic thin film transistor-forming composition can be preferably used in the organic thin film transistor. The method of manufacturing the organic thin film transistor includes a step of forming an organic semiconductor film by applying the organic thin film transistor-forming composition to a substrate.

4 Claims, 5 Drawing Sheets

Related U.S. Application Data continuation of application No. PCT/JP2017/023233, filed on Jun. 23, 2017.

(51) Int. Cl.
    *C07D 471/22*    (2006.01)
    *C07D 491/22*    (2006.01)
    *H01L 29/786*    (2006.01)
    *H10K 10/84*    (2023.01)
    *H10K 10/46*    (2023.01)

(52) U.S. Cl.
    CPC .......... *C07D 491/22* (2013.01); *H01L 29/786* (2013.01); *H10K 10/84* (2023.02); *H10K 85/621* (2023.02); *H10K 85/6574* (2023.02); *H10K 10/464* (2023.02); *H10K 10/466* (2023.02); *H10K 10/484* (2023.02)

(58) Field of Classification Search
    CPC ............. H01L 51/0588; H01L 51/0073; H01L 51/105; H01L 29/786
    USPC .......................................................... 257/40
    See application file for complete search history.

(56) References Cited

U.S. PATENT DOCUMENTS

| | | |
|---|---|---|
| 8,796,672 B2 | 8/2014 | Facchetti et al. |
| 2008/0054258 A1 | 3/2008 | Koenemann et al. |
| 2008/0185577 A1 | 8/2008 | Facchetti et al. |
| 2010/0283047 A1 | 11/2010 | Facchetti et al. |
| 2010/0319778 A1 | 12/2010 | Kastler et al. |
| 2011/0155247 A1 | 6/2011 | Quinn et al. |
| 2013/0284265 A1 | 10/2013 | Jiang et al. |
| 2019/0131546 A1 | 5/2019 | Fukuzaki et al. |

FOREIGN PATENT DOCUMENTS

| | | |
|---|---|---|
| EP | 3379590 A1 | 9/2018 |
| JP | 2008541440 A | 11/2008 |
| JP | 2009179794 A | 8/2009 |
| JP | 2010500745 A | 1/2010 |
| JP | 2010-510228 A | 4/2010 |
| JP | 2012-176967 A | 9/2012 |
| JP | 2014508132 A | 4/2014 |
| JP | 6555667 B2 | 8/2019 |
| TW | 201000512 A | 1/2010 |
| WO | 2006120143 A1 | 11/2006 |
| WO | 2008/017714 A1 | 2/2008 |
| WO | 2009/098252 A1 | 8/2009 |
| WO | 2011/082234 A1 | 7/2011 |
| WO | 2014/100961 A1 | 7/2014 |
| WO | 2017/086320 A1 | 5/2017 |

OTHER PUBLICATIONS

Gallaher et al., Controlled aggregation of peptide-substituted perylene-bisimides, Chem. Commun., 2012, 48, 7961-7963, Jun. 13, 2012.
International Search Report issued in PCT/JP2017/023233; mailed Aug. 29, 2017.
Written Opinion of the International Searching Authority issued in PCT/JP2017/023233; mailed Aug. 29, 2017.
Heinz Langhals and Susanne Kirner, "Novel Fluorescent Dyes by the Extension of the Core of Perylenetetracarboxylic Bisimides", European Journal of Organic Chemistry, Jan. 1, 2000, pp. 365-380.
Extended European Search Report issued by the European Patent Office on Apr. 2, 2019, which corresponds to EP17820058.0—1110 and is related to U.S. Appl. No. 16/224,903.
An Office Action mailed by the Japanese Patent Office on Aug. 4, 2020, which corresponds to Japanese Patent Application No. 2019-119301 and is related to U.S. Appl. No. 16/224,903 with English language translation.
Zhurnal Organicheskoi Khimii; 1992; pp. 2301-2309; vol. 28 (11).
An Office Action mailed by the Japanese Patent Office on Jun. 4, 2019, which corresponds to Japanese Patent Application No. 2017-122786 and is related to U.S. Appl. No. 16/224,903.
An Office Action mailed by the European Patent Office on Dec. 2, 2019, which corresponds to European Patent Application No. 17820058.0—1110 and is related to U.S. Appl. No. 16/224,903.
An Office Action mailed by Taiwanese Patent Office on Oct. 6, 2020, which corresponds to Taiwanese Patent Application No. 106121310 and is related to U.S. Appl. No. 16/224,903; with English language translation.

\* cited by examiner (A)

(B)

(C)

ORGANIC THIN FILM TRANSISTOR, ORGANIC SEMICONDUCTOR FILM, COMPOUND, ORGANIC THIN FILM TRANSISTOR-FORMING COMPOSITION, AND METHOD OF MANUFACTURING ORGANIC THIN FILM TRANSISTOR

CROSS-REFERENCE TO RELATED APPLICATIONS

This application is a Divisional of application Ser. No. 16/224,903 filed on Dec. 19, 2018, which is a Continuation of PCT International Application No. PCT/JP2017/023233 filed on Jun. 23, 2017, which claims priorities under 35 U.S.C. § 119 (a) to Japanese Patent Applications JP2016-126449 filed on Jun. 27, 2016 and JP2017-122786 filed on Jun. 23, 2017. Each of the above applications is hereby expressly incorporated by reference, in its entirety, into the present application.

BACKGROUND OF THE INVENTION

1. Field of the Invention

The present invention relates to an organic thin film transistor, an organic semiconductor film, a compound, an organic thin film transistor-forming composition, and a method of manufacturing an organic thin film transistor.

2. Description of the Background Art

In a display such as a liquid crystal display or an organic electroluminescence display, a device using a logical circuit such as a radio frequency identifier (RFID) or a memory, or the like, a transistor is used. In particular, an organic thin film transistor including an organic semiconductor film can realize weight reduction or cost reduction and also has excellent flexibility. Therefore, the organic thin film transistor including an organic semiconductor film is superior to an inorganic transistor including an inorganic semiconductor film.

Examples of the organic compound including an organic semiconductor film include perylene bisimide (also referred to as thionated perylene bisimide) in which at least one carbonyl group in an imido group is converted into a thiocarbonyl group (WO2011/082234A). Chemical Communications, 2012, 48, p. 7961-7963 describes a method of synthesizing perylene bisimide which is a synthesis raw material of thionated perylene bisimide.

SUMMARY OF THE INVENTION

The performance of the above-described display or the like has rapidly progressed, and improvement of initial performance (carrier mobility) is required for an organic thin film transistor to be mounted on the display or the like. In addition, in the above-described display or the like, in order to satisfy requirements for cost reduction or flexibility, a property (durability) capable of realizing stable driving in the atmosphere and maintaining high performance is desired even without providing a special protective layer or sealing layer.

However, in an organic thin film transistor of the related art such as an organic thin film transistor including the compound described in WO2011/082234A, the performance tends to largely deteriorate in the atmosphere, and there is room for improvement from the viewpoints of initial performance and durability.

An object of the present invention is to provide an organic thin film transistor that maintains a high carrier mobility even in the atmosphere and a method of manufacturing the organic thin film transistor. In addition, another object of the present invention is to provide an organic semiconductor film, a compound, and an organic thin film transistor-forming composition that can be preferably used in the organic thin film transistor having the above-described properties.

As a result of a thorough investigation, the present inventors found that a compound represented by specific Formula (1) described below can be preferably used as an organic semiconductor in an organic thin film transistor, and also found that, by adding this compound to an organic semiconductor film, a high carrier mobility is exhibited and deterioration in carrier mobility can be suppressed even in the atmosphere. The present invention has been completed based on the above findings as a result of repeated investigation.

The object of the present invention is achieved by the following means.

<1> An organic thin film transistor comprising:

an organic semiconductor film that includes a compound represented by the following Formula (1),

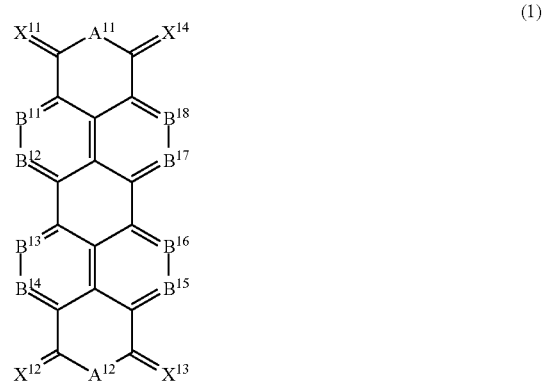

in Formula (1), $A^{11}$ and $A^{12}$ each independently represent —O—, —N($R^N$)—, or —P($R^N$)—, $B^{11}$ to $B^{18}$ each independently represent —N= or —C($R^M$)=, at least one of $B^{11}$, . . . , or $B^{18}$ represents —N=, $R^N$ and $R^M$ represent a hydrogen atom or a substituent, and $X^{11}$ to $X^{14}$ each independently represent an oxygen atom or a sulfur atom.

<2> The organic thin film transistor according to <1>, in which the compound is represented by the following Formula (2),

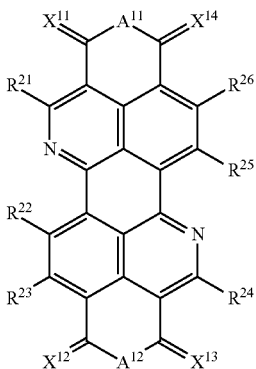

(2)

in Formula (2), $A^{11}$ and $A^{12}$ have the same definitions as $A^{11}$ and $A^{12}$ in Formula (1), $X^{11}$ to $X^{14}$ have the same definitions as $X^{11}$ to $X^{14}$ in Formula (1), and $R^{21}$ to $R^{26}$ each independently represent a hydrogen atom or a substituent.

<3> The organic thin film transistor according to <1> or <2>, in which all of $X^{11}$ to $X^{14}$ represent an oxygen atom.

<4> The organic thin film transistor according to any one of <1> to <3>, in which both $A^{11}$ and $A^{12}$ represent —N($R^N$)—, and $R^N$ represents a hydrogen atom or a substituent.

<5> The organic thin film transistor according to any one of <1> to <4>, in which $R^N$ represents an alkyl group having 1 to 20 carbon atoms, an aryl group having 6 to 20 carbon atoms, or a heteroaryl group having 3 to 20 carbon atoms as ring-constituting atoms.

<6> A compound represented by the following Formula (2),

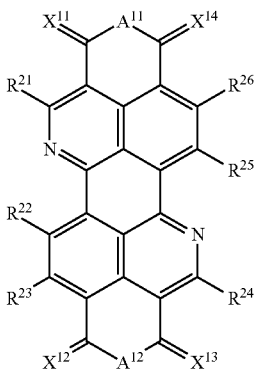

(2)

in Formula (2), $A^{11}$ and $A^{12}$ each independently represent —O—, —N($R^N$)—, or —P($R^N$)—, $R^N$ represents a hydrogen atom or a substituent, $R^{21}$ to $R^{26}$ each independently represent a hydrogen atom or a substituent, and $X^{11}$ to $X^{14}$ each independently represent an oxygen atom or a sulfur atom.

<7> The compound according to <6>, in which all of $X^{11}$ to $X^{14}$ represent an oxygen atom.

<8> The compound according to <6> or <7>, in which both $A^{11}$ and $A^{12}$ represent —N($R^N$)—, and $R^N$ represents a hydrogen atom or a substituent.

<9> The compound according to any one of <6> to <8>, in which $R^N$ represents an alkyl group having 1 to 20 carbon atoms, an aryl group having 6 to 20 carbon atoms, or a heteroaryl group having 3 to 20 carbon atoms as ring-constituting atoms.

<10> An organic thin film transistor-forming composition comprising:

the compound according to any one of <6> to <9>.

<11> The organic thin film transistor-forming composition according to <10> further comprising:

a binder polymer.

<12> An organic semiconductor film comprising:

a compound represented by the following Formula (1),

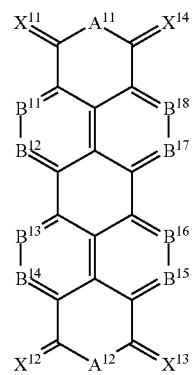

(1)

in Formula (1), $A^{11}$ and $A^{12}$ each independently represent —O—, —N($R^N$)—, or —P($R^N$)—, $B^{11}$ to $B^{18}$ each independently represent —N= or —C($R^M$)=, at least one of $B^{11}$, . . . , or $B^{18}$ represents —N=, $R^N$ and $R^M$ represent a hydrogen atom or a substituent, and $X^{11}$ to $X^{14}$ each independently represent an oxygen atom or a sulfur atom.

<13> A method of manufacturing an organic thin film transistor, the method comprising:

a step of forming an organic semiconductor film by applying the organic thin film transistor-forming composition according to <10> or <11> to a substrate.

According to the present invention, it is possible to provide an organic thin film transistor that maintains a high carrier mobility even in the atmosphere and a method of manufacturing the organic thin film transistor. In addition, according to the present invention, it is also possible to provide an organic semiconductor film, a compound, and an organic thin film transistor-forming composition that can be preferably used in the organic thin film transistor having the above-described properties.

The above-described and other characteristics and advantageous effects of the present invention will be clarified from the following description appropriately with reference to the accompanying drawings.

DESCRIPTION OF THE PREFERRED EMBODIMENTS

Figure 1:
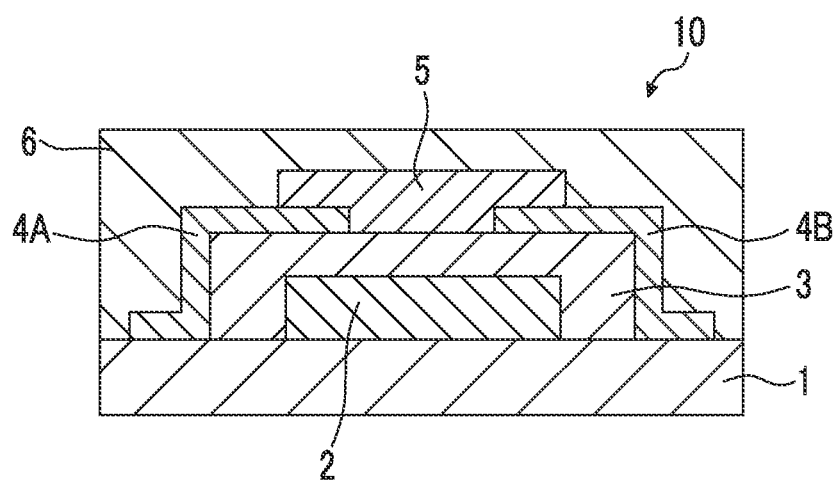
FIG. 1 is schematic cross-sectional view showing a bottom gate-bottom contact type organic thin film transistor that is an example of an organic thin film transistor according to an embodiment of the present invention.

In this specification, numerical ranges represented by "to" include numerical values before and after "to" as lower limit values and upper limit values.

The meaning of compounds described in this specification include not only the compounds themselves but also salts and ions thereof. In addition, within a range where a desired effect does not deteriorate, a part of the structure may be changed.

In addition, in a case where it is not clearly described that a compound is substituted or unsubstituted, this compound has any substituent within a range where a desired effect does not deteriorate. The same shall be applied to a substituent, a linking group, or the like (hereinafter, referred to as "substituent or the like").

In this specification, in a case where a plurality of substituents or the like represented by a specific reference numeral are present or a plurality of substituents or the like are simultaneously defined, the respective substituents or the like may be the same as or different from each other unless specified otherwise. The same shall be applied to definition of the number of substituents or the like. In addition, in a case where a plurality of substituents or the like are close to (in particular, adjacent to) each other, the substituents or the like may be linked to each other to form a ring unless specified otherwise.

In the present invention, in a case where the number of carbon atoms in a group is limited, the number of carbon atoms in this group represents the total number of carbon atoms including substituents unless specified otherwise.

In the present invention, in a case where a group can form an acyclic skeleton and a cyclic skeleton, this group includes a group having an acyclic skeleton and a group having a cyclic skeleton unless specified otherwise. For example, an alkyl group includes a linear alkyl group, a branched alkyl group, and a cycloalkyl group. In a case where a group can form a cyclic skeleton, the lower limit of the number of atoms of the group forming a cyclic skeleton is not limited to the lower limit of the number of atoms specifically described regarding this group, and is 3 or more and preferably 5 or more. The cycloalkyl group represents a bicycloalkyl group, a tricycloalkyl group, or the like.

A preferable embodiment of the present invention will be described below, but the present invention is not limited thereto.

[Compound Represented by Formula (1)]

First, a compound represented by Formula (1) according to an embodiment of the present invention (hereinafter, also referred to as "the compound according to the embodiment of the present invention") will be described.

With an organic semiconductor film including the compound according to the embodiment of the present invention, high carrier mobility and durability capable of maintaining the high carrier mobility even in the atmosphere can be imparted to an organic thin film transistor. The reason for this is not clear but is presumed to be as follows. The compound according to the embodiment of the present invention has a structure in which at least one carbon atom which forms a 3,4,9,10-perylene bisimide skeleton is substituted with a nitrogen atom. With this structure, the orbital energy of the lowest unoccupied molecular orbital (LUMO) is lower than −4.0 eV even without further fusing an aromatic ring to the perylene bisimide skeleton (without extending the π-conjugated system). As a result, it is presumed that n-type semiconductor properties are improved. In addition, it is presumed that even in a case where the organic semiconductor film is exposed to oxygen gas or water in the atmosphere, deterioration of the organic semiconductor film caused by oxygen gas or water (for example, decomposition of the compound according to the embodiment of the present invention) can be effectively suppressed. Therefore, even in a case where the compound according to the embodiment of the present invention is used for an organic thin film transistor, the carrier mobility can be improved to a high level, and deterioration over time in the atmosphere can be suppressed.

The compound according to the embodiment of the present invention having the above-described properties and actions is not particularly limited to the above-described use and is applicable, for example, a non-light-emitting organic semiconductor device. The non-light-emitting organic semiconductor device refers to a device that is not made to emit light. Examples of the device include an organic thin film transistor that controls a current amount or a voltage amount, an organic photoelectric conversion element (for example, a solid image pickup element for an optical sensor or a solar cell for energy conversion) that converts light energy into electric power, an organic thermoelectric conversion element that converts thermal energy into electric power, a gas sensor, an organic rectifying element, an organic inverter, and an information recording element. As described below, the compound according to the embodiment of the present invention is preferably used as an organic semiconductor material of the organic thin film transistor.

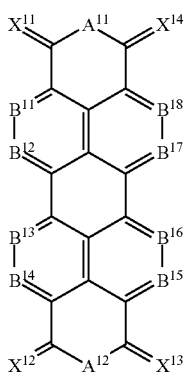

(1)

In Formula (1), $A^{11}$ and $A^{12}$ each independently represent —O—, —N($R^N$)—, or —P($R^N$)—. It is preferable that $A^{11}$ and $A^{12}$ each independently represent —N($R^N$)—. $A^{11}$ and $A^{12}$ may be the same as or different from each other but are preferably the same as each other. It is more preferable that both $A^{11}$ and $A^{12}$ represent —N($R^N$)—.

$R^N$ represents a hydrogen atom or a substituent.

The substituent which may be used as $R^N$ is not particularly limited. Examples of the substituent include groups selected from the following substituent group Z.

Substituent Group Z

The substituent group Z includes:
- a halogen atom (for example, a fluorine atom, a chlorine atom, a bromine atom, and an iodine atom; among these, a fluorine atom or a chlorine atom is preferable);
- an alkyl group (preferably having 1 (3) to 40 carbon atoms, more preferably 1 (3) to 20 carbon atoms, still more preferably 4 to 20 carbon atoms, wherein a numerical value in parentheses represents the number of carbon atoms in the case of a cycloalkyl group; examples of the alkyl group include methyl, ethyl, propyl, 2-methylpropyl, butyl, amyl, pentyl, 2,2-dimethylpropyl, hexyl, heptyl, octyl, nonyl, decyl, undecyl, dodecyl, tridecyl, tetradecyl, pentadecyl, 2,6-dimethyloctyl, icosyl, 2-decyltetradecyl, 2-hexyldodecyl, 2-ethyloctyl, 2-butyldecyl, 1-octylnonyl, 2-ethyloctyl, 2-octyldecyl, 2-octyldodecyl, 7-hexylpentadecyl, 2-octyltetradecyl, 2-ethylhexyl, cyclopropyl, cyclobutyl, cyclopentyl, cyclohexyl, adamantyl, benzyl, p-chlorobenzyl, trifluoromethyl, perfluoroethyl, 2,2,3,3,4,4,4-perfluorobutyl, $C_5F_{11}C_2H_4$—, 3-aminopropyl, 4-aminobutyl, 5-ethoxypentyl, (meth)acryloxypropyl, (meth)acryloxypentyl, 4-hydroxybutyl, 4-sulfobutyl, 10-phosphonodecyl, 2-hydroxyethoxymethyl, 2-imidazolylethoxymethyl, and 4-(N,N-dimethylamino)butyl);
- an alkenyl group (having preferably 2 to 20 carbon atoms, more preferably 2 to 12 carbon atoms, and still more preferably 2 to 8 carbon atoms; for example, vinyl, allyl, 2-butenyl, 1-pentenyl, or 4-pentenyl);
- an alkynyl group (having preferably 2 to 20 carbon atoms, more preferably 2 to 12 carbon atoms, and still more preferably 2 to 8 carbon atoms; for example, propargyl, 1-pentynyl, trimethylsilylethynyl, triethylsilylethynyl, tri-i-propylsilylethynyl, or 2-p-propylphenylethynyl);
- an aryl group (preferably 6 to 20 carbon atoms and more preferably 6 to 12 carbon atoms, for example, phenyl, naphtyl, 2,4,6-trimethylphenyl, p-(t-butyl)phenyl, 4-methyl-2,6-dipropylphenyl, 4-fluorophenyl, 4-trifluoromethylphenyl, p-pentylphenyl, 3,4-dipentylphenyl, p-heptoxyphenyl, or 3,4-diheptoxyphenyl);
- a heterocyclic group (including at least one heteroatom and 1 to 30 carbon atoms as ring-constituting atoms; examples of the heteroatom include a nitrogen atom, an oxygen atom, and a sulfur atom; the number of heteroatoms is not particularly limited and is, for example, 1 or 2; the number of ring-constituting carbon atoms is preferably 3 to 20 and more preferably 3 to 12; as the heterocyclic group, a 5-membered ring, a 6-membered ring, or a fused ring thereof is preferable; the heterocyclic group represents an aromatic heterocyclic group (heteroaryl group) or an aliphatic heterocyclic group; examples of the heterocyclic group include thienyl, thiazolyl, imidazolyl, pyridyl, pyrimidinyl, quinolyl, furanyl, selenophenyl ($C_4H_3Se$), piperidyl, morpholino, benzoxazolyl, benzimidazolyl, benzothiazolyl, 2-hexylfuranyl, and pyranyl);
- a silyl group (having preferably from 3 to 40 carbon atoms, more preferably from 3 to 30 carbon atoms, and still more preferably from 3 to 24 carbon atoms; for example, trimethylsilyl, triphenylsilyl, or dimethylphenylsilyl);
- an alkoxy group (having preferably 1 to 20 carbon atoms, more preferably 1 to 12 carbon atoms, and still more preferably 1 to 8 carbon atoms; for example, methoxy, ethoxy, or butoxy);
- an amino group (having preferably 0 to 20 carbon atoms, more preferably 0 to 10 carbon atoms, still more preferably 0 to 6 carbon atoms; for example, amino, methylamino, dimethylamino, diethylamino, dibenzylamino, or anilino);
- an aryloxy group (having preferably 6 to 20 carbon atoms, more preferably 6 to 16 carbon atoms, and still more preferably 6 to 12 carbon atoms; for example, phenyloxy or 2-naphtyloxy);
- an acyl group (having preferably from 1 to 20 carbon atoms, more preferably from 1 to 16 carbon atoms, and still more preferably from 1 to 12 carbon atoms; for example, acetyl, hexanoyl, benzoyl, formyl or pivaloyl);
- an alkoxycarbonyl groups (having preferably from 2 to 20 carbon atoms, more preferably from 2 to 16 carbon atoms, and still more preferably from 2 to 12 carbon atoms; for example, methoxycarbonyl or ethoxycarbonyl);
- an aryloxycarbonyl group (having preferably from 7 to 20 carbon atoms, more preferably from 7 to 16 carbon atoms, and still more preferably from 7 to 10 carbon atoms; for example, phenyloxycarbonyl);
- an acyloxy group (having preferably from 2 to 20 carbon atoms, more preferably from 2 to 16 carbon atoms, and still more preferably from 2 to 10 carbon atoms; for example, acetoxy, benzoyloxy, (meth)acryloyloxy);
- an acylamino group (having preferably from 2 to 20 carbon atoms, more preferably from 2 to 16 carbon atoms, and still more preferably from 2 to 10 carbon atoms; for example, acetylamio or benzoylamino);
- an aminocarbonylamino group (having 2 to 20 carbon atoms, more preferably 2 to 16 carbon atoms, and still more preferably 2 to 12 carbon atoms, for example, an ureido group);
- an alkoxy or aryloxycarbonylamino group (having preferably 2 (7) to 20 carbon atoms, more preferably 2 (7) to 16 carbon atoms, and still more preferably 2 (7) to 12 carbon atoms; a numerical value in parentheses represents the number of carbon atoms in the aryloxycarbonylamino group; for example, methoxycarbonylamino or phenyloxycarbonylamino);
alkyl or arylsulfonylamino;
an alkylthio group (having preferably from 1 to 20 carbon atoms, more preferably from 1 to 16 carbon atoms, and still more preferably from 1 to 12 carbon atoms; for example, methylthio, ethylthio, or octylthio);
an arylthio group (having preferably from 6 to 20 carbon atoms, more preferably from 6 to 16 carbon atoms, and still more preferably from 6 to 12 carbon atoms; for example, a phenylthio group);
an alkyl or arylsulfinyl group;
an alkyl or arylsulfonyl group;
a silyloxy group;
a heterocyclic oxy group;
a carbamoyl group;
a carbamoyloxy group;
a heterocyclic thio group;
a sulfamoyl group;
an aryl or heterocyclic azo group;
an imido group;
a phosphino group;
a phosphinyl group;
a phosphinyloxy group;
a phosphinylamino group;
a hydrazino group;
an imino group;
a cyano group;
a hydroxy group;
a nitro group;
a mercapto group;
a sulfo group;
a carboxy group;
a hydroxamic acid group;
a sulfino group;
a boronic acid group (—B(OH)$_2$);
a phosphate group (—OPO(OH)$_2$);
a phosphono group (—PO(OH)$_2$); and
a sulfate group (—OSO$_3$H).

Among these, as a group which may be selected as $R^N$ from the substituent group Z, an alkyl group, an aryl group, an alkenyl group, an alkynyl group, a heterocyclic group, or a silyl group is preferable, an alkyl group (preferably having 1 to 20 carbon atoms), an aryl group (preferably having 6 to 20 carbon atoms), or a heteroaryl group (including at least one heteroatom as a ring-constituting atom; preferably a 5-membered ring, a 6-membered ring, or a fused ring thereof, the number of ring-constituting carbon atoms is 3 to 20) is more preferable, and an alkyl group (having more preferably 4 to 20) is still more preferable.

The group selected from the substituent group Z may further have a substituent. Examples of the substituent include groups selected from the substituent group Z.

In the group which may further have a substituent (also referred to as "group including a combination of substituents"), the number of substituents which may be further included is, for example, preferably 1 to 6 and more preferably 1 to 3.

The group including a combination of substituents is not particularly limited, and examples thereof include a group obtained by substituting each of the preferable groups selected from the substituent group Z with another group selected from the substituent group Z. Specific examples of the group including a combination of substituents include an alkyl group having, as a substituent, a group selected from the group consisting of a halogen atom, an alkyl group, an aryl group, a heterocyclic group (heteroaryl group), an alkoxy group (for example, a hydroxyalkoxy group, an alkoxy halide group, or a heteroalkoxy group), an amino group, an acyloxy group, a hydroxy group, a sulfate group, and a phosphono group, an aryl halide group, and an alkynyl group having an aryl halide group or a (fluorinated) alkyl aryl group, a silyl group as a substituent. Further, a group obtained by removing one hydrogen atom from the compound represented by Formula (1) may be used.

More specifically, a group described as the examples of the substituent group Z, an exemplary compound described below, or a group in a compound used in Examples below may be used.

Among these, as the group including a combination of substituents, an alkyl group (alkyl halide group) having a halogen atom as a substituent or an alkyl group having an aryl group as a substituent is preferable, an alkyl group (alkyl fluoride group) having a fluorine atom as a substituent or an alkyl group having an aryl group as a substituent is more preferable, and an alkyl group having an aryl group as a substituent is still more preferable.

As the substituent which may be used as $R^N$, a (unsubstituted) alkyl group or an alkyl group having an alkyl halide group or an aryl group as a substituent is more preferable.

In a case where $A^{11}$ and $A^{12}$ independently represent $R^N$, two $R^N$'s may be the same as or different from each other.

In Formula (1), $B^{11}$ to $B^{18}$ each independently represent —N= or —C($R^M$)=. Here, $R^M$ represents a hydrogen atom or a substituent and preferably a hydrogen atom.

A substituent which may be used as $R^M$ is not particularly limited, and examples thereof include groups selected from the substituent group Z. The group selected from the substituent group Z may further have a substituent. Examples of the substituent include groups selected from the substituent group Z. Examples of a group which may further have a substituent include the above-described examples of the group including a combination of substituents which may be used as $R^N$. Specifically, the above-described group and further a methine group bonded to a carbon atom of the compound represented by Formula (1) may be used.

Among these, as the substituent which may be used as $R^M$, an alkyl group, an alkenyl group, an alkoxycarbonyl group, an aryl group, an alkoxy group, a heterocyclic group (in particular, heteroaryl group), an amino group, a halogen atom, a cyano group, a carboxy group, a nitro group, or a mercapto group is preferable, an alkyl group, an alkenyl group, an aryl group, an alkoxy group, a heterocyclic group (in particular, heteroaryl group), a halogen atom, or a cyano group is more preferable, and an alkyl group, an aryl group, a heterocyclic group (in particular, heteroaryl group), a halogen atom, or a cyano group is still more preferable.

The substituent which may be used as $R^M$ may form a ring. Examples of an aspect where the substituent forms a ring include an aspect where the substituents are bonded to each other to form a ring and an aspect where one atom is shared by a plurality of substituents to form a ring.

Examples of the aspect where the substituents are bonded to each other to form a ring include an aspect where two vinyl groups are bonded to each other to form a benzene ring together with a carbon atom bonded to $R^M$. In addition, examples of the aspect where one atom is shared by a plurality of substituents to form a ring include an aspect where two substituents are combined to form a sulfur atom (—S— group).

At least one of $B^{11}$, . . . , or $B^{18}$ represents —N=, it is preferable that one to four of $B^{11}$ to $B^{18}$ represent —N=, it is more preferable that one or two of $B^{11}$ to $B^{18}$ represent —N=, and it is more preferable that two of $B^{11}$ to $B^{18}$ represent —N=.

B which may be used —N= is not particularly limited, and any one of $B^{11}$, . . . , or $B^{18}$ may represent —N=. For example, it is preferable that at least one of $B^{12}$, $B^{13}$, $B^{16}$, or $B^{17}$ represents —N=. It is more preferable that any one or both of $B^{12}$ and $B^{16}$ represent —N=.

In —N= which may be used as $B^{11}$ to $B^{18}$, a nitrogen atom may have a substituent. For example, an N-oxide group (N→O group) or a salt having a counter anion may be used.

In Formula (1), it is preferable that $X^{11}$ to $X^{14}$ each independently represent an oxygen atom or a sulfur atom and preferably an oxygen atom. It is more preferable all of $X^{11}$ to $X^{14}$ represents an oxygen atom.

Here, combinations of $A^{11}$ and $A^{12}$ with $X^{11}$ to $X^{14}$ are not particularly limited, and a combination in which $A^{11}$ and $A^{12}$ represent —N($R^N$)— and $X^{11}$ to $X^{14}$ represent an oxygen atom is preferable.

It is preferable that the compound represented by Formula (1) is represented by the following Formula (2).

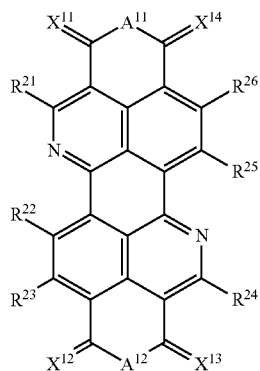

(2)

In Formula (2), $A^{11}$, $A^{12}$, and $X^{11}$ to $X^{14}$ have the same definitions and the same preferable ranges as $A^{11}$, $A^{12}$, and $X^{11}$ to $X^{14}$ in Formula (1), respectively. In addition, preferable combinations of A, $A^{12}$, and $X^{11}$ to $X^{14}$ are as described above.

$R^{21}$ to $R^{26}$ each independently represent a hydrogen atom or a substituent. A substituent which may be used as $R^{21}$ to $R^{26}$ has the same definition and the same preferable range as the substituent which may be used as $R^M$. $R^M$'s may be bonded to each other, or $R^M$ may be bonded to a carbon atom which forms an isoquinolino quinoline skeleton to form a ring.

Specific examples of the compound represented by Formula (1) will be shown below and in Examples, but the present invention is not limited thereto.

In the following specific examples, compounds in which both $A^{11}$ and $A^{12}$ represent —N($R^N$)— are shown. However, in the following specific examples, compounds in which any one or both of $A^{11}$ and $A^{12}$ (N—$R^{N1}$ and N—$R^{N2}$ in the following specific examples) are substituted with —O— or —P($R^N$)— may be used. Here, examples of $R^N$ in —P($R^N$)— include the same groups as $R^{N1}$ or $R^{N2}$ in the following specific examples.

In the following specific examples, TIPS represents a triisopropylsilyl group, and * represents a binding site.

| No. | $X^1$ | $X^2$ | $X^3$ | $X^4$ | $R^{21}$ | $R^{27}$ | $R^{22}$ | $R^{23}$ | $R^{24}$ | $R^{25}$ | $R^{26}$ | $R^{N1}$ | $R^{N2}$ |
|---|---|---|---|---|---|---|---|---|---|---|---|---|---|
| 1 | O | O | O | O | H | H | H | H | H | H | H | H | H |
| 2 | O | O | O | O | H | H | H | H | H | H | H | $CH_3$ | $C_3$ |
| 3 | O | O | O | O | H | H | H | H | H | H | H | $nC_6H_{13}$ | $nC_6H_{13}$ |
| 4 | O | O | O | O | H | H | H | H | H | H | H | cyclohexyl* | cyclohexyl* |
| 5 | S | O | O | O | H | H | H | H | H | H | H | cyclohexyl* | cyclohexyl* |
| 6 | O | S | S | S | H | H | H | H | H | H | H | cyclohexyl* | cyclohexyl* |
| 7 | O | S | S | O | H | H | H | H | H | H | H | cyclohexyl* | cyclohexyl* |
| 8 | O | O | O | O | H | H | H | H | H | H | H | $CH_2C_3F_7$ | $CH_2C_3F_7$ |
| 9 | O | O | O | O | H | H | H | H | H | H | H | -isoPropyl | -isoPropyl |
| 10 | O | O | O | O | H | H | H | H | H | H | H | -tert-Butyl | -tert-Butyl |

| | | | | | | | | | |
|---|---|---|---|---|---|---|---|---|---|
| 11 | S | S | O | O | H | H | H | H | H | H | ![C8H17/C8H17 branched] | ![C8H17/C8H17 branched] |
| 12 | O | O | O | O | H | H | H | H | H | H | ![C8H17/C8H17 branched] | ![C8H17/C10H21 branched] |
| 13 | O | O | O | O | H | H | H | H | H | H | ![C2H4C5F11] | ![C2H4C5F11] |
| 14 | O | O | O | O | Cl | Cl | Cl | Cl | Cl | Cl | ![cyclohexyl] | ![cyclohexyl] |
| 15 | O | O | O | O | H | H | H | F | H | H | ![phenyl] | ![phenyl] |
| 16 | O | O | O | O | F | F | F | F | F | F | ![mesityl] | ![mesityl] |
| 17 | O | O | O | O | CN | CN | H | H | H | F | ![neopentyl] | ![isobutyl] |
| 18 | O | O | O | O | Br | H | H | H | H | H | ![branched nC6H13/nC8H17] | ![mesityl] |
| 19 | O | O | O | O | NO₂ | H | H | H | H | H | ![cyclobutyl] | ![cyclopropyl] |

-continued

| | | | | | | | | | | | |
|---|---|---|---|---|---|---|---|---|---|---|---|
| 20 | O | O | O | O | $CH_3$ | $nC_6H_{13}$ | H | H | H | benzyl (–CH$_2$–C$_6$H$_5$) | 4-chlorobenzyl |
| 21 | O | O | O | O | $CO_2CH_3$ | H | H | H | H | 1-adamantyl | 1-adamantyl |
| 22 | O | O | O | O | H | -Ph | -Ph | H | H | cyclopentyl | cyclopentyl |
| 23 | O | O | O | O | —COOH | H | H | H | H | $CF_2$ | $C_2F_5$ |
| 24 | O | O | O | O | H | $CF_3$ | H | H | H | 3,5-diisopropyl-4-methylphenyl | 4-tert-butylphenyl |
| 25 | O | O | O | O | $OCH_3$ | H | H | H | H | 4-ethoxybutyl | 4-aminobutyl |

-continued
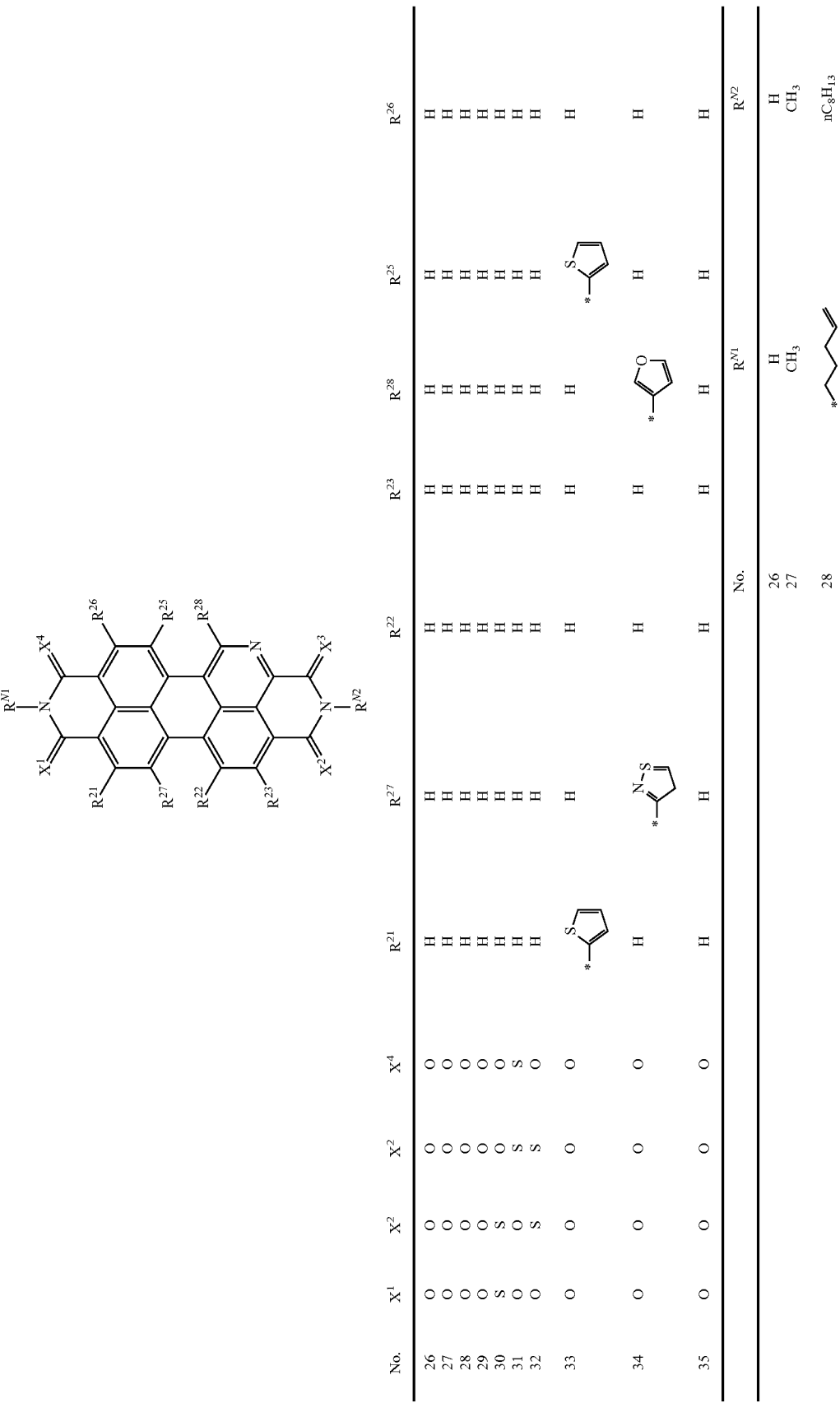
| No. | $X^1$ | $X^2$ | $X^3$ | $X^4$ | $R^{21}$ | $R^{27}$ | $R^{22}$ | $R^{23}$ | $R^{28}$ | $R^{25}$ | $R^{26}$ |
|---|---|---|---|---|---|---|---|---|---|---|---|
| 26 | O | O | O | O | H | H | H | H | H | H | H |
| 27 | O | O | O | O | H | H | H | H | H | H | H |
| 28 | O | O | O | O | H | H | H | H | H | H | H |
| 29 | S | S | S | O | H | H | H | H | H | H | H |
| 30 | O | O | O | S | H | H | H | H | H | H | H |
| 31 | O | S | S | S | H | H | H | H | H | H | H |
| 32 | O | S | S | O | H | H | H | H | H | H | H |
| 33 | O | O | O | O | | | H | H | | | H |
| 34 | O | O | O | O | H | H | H | H | H | H | H |
| 35 | O | O | O | O | H | H | H | H | H | H | H |
| No. | $R^{N1}$ | $R^{N2}$ |
|---|---|---|
| 26 | H | H |
| 27 | $CH_3$ | $CH_3$ |
| 28 | | $nC_8H_{13}$ |

-continued

| No. | | |
|---|---|---|
| 29 | cyclohexyl-* | cyclohexyl-* |
| 30 | nC₁₀H₂₁-cyclohexyl-* | nC₁₀H₂₁-cyclohexyl-* |
| 31 | tetrahydropyran-2-yl-* | tetrahydropyran-2-yl-* |
| 32 | CH₂C₃F₇ | methyl vinyl ketone chain with -isoPropyl |
| 33 | -isoPropyl | |
| 34 | *—SO₃H | *—OH |
| 35 | | |

[Structure of polycyclic aromatic compound with R²¹–R²⁶, X¹–X⁴, Rᴺ¹, Rᴺ² substituents]

| No. | X¹ | X² | X³ | X⁴ | R²¹ | R²² | R²³ | R²⁴ | R²⁵ | R²⁶ | Rᴺ¹ | Rᴺ² |
|---|---|---|---|---|---|---|---|---|---|---|---|---|
| 36 | O | O | O | O | H | H | H | H | H | H | H | H |
| 37 | O | O | O | O | H | H | H | H | H | H | CH₃ | CH₃ |
| 38 | O | O | O | O | H | H | H | H | H | H | nC₆H₁₃ | nC₆H₁₃ |

-continued

| No. | | | | | | | | | | | | |
|---|---|---|---|---|---|---|---|---|---|---|---|---|
| 39 | O | O | O | O | H | H | H | H | H | H | cyclohexyl | cyclohexyl |
| 40 | S | S | O | O | H | H | H | H | H | H | cyclohexyl | cyclohexyl |
| 41 | O | O | S | S | H | H | H | H | H | H | phenyl | phenyl |
| 42 | O | S | S | O | H | H | H | H | H | H | 4-CF$_3$-phenyl | 4-CF$_3$-phenyl |
| 43 | O | O | O | O | H | H | H | H | H | H | CH$_2$C$_3$F$_7$ | CH$_2$C$_3$F$_7$ |
| 44 | O | O | O | O | H | H | H | H | H | H | -isoPropyl | -isoPropyl |
| 45 | O | O | O | O | H | H | H | H | H | H | -tert-Butyl | -tert-Butyl |
| 46 | S | S | S | O | H | H | H | H | H | H | CH$_2$CH(C$_8$H$_{17}$)C$_8$H$_{17}$ | CH$_2$CH(C$_8$H$_{17}$)C$_8$H$_{17}$ |
| 47 | O | O | O | O | H | H | H | H | H | H | CH$_2$CH(C$_8$H$_{17}$)C$_{10}$H$_{21}$ | CH$_2$CH(C$_8$H$_{17}$)C$_8$H$_{17}$ |
| 48 | O | O | O | O | H | H | H | H | H | H | C$_2$H$_4$C$_5$F$_{11}$ | C$_2$H$_4$C$_5$F$_{11}$ |
| 49 | O | O | O | O | Cl | Cl | Cl | Cl | Cl | Cl | cyclohexyl | cyclohexyl |
| 50 | O | O | O | O | H | F | H | H | F | H | phenyl | phenyl |

-continued

| # | | | | | | | | | | | |
|---|---|---|---|---|---|---|---|---|---|---|---|
| 51 | O | O | O | F | F | F | F | F | F | mesityl | mesityl |
| 52 | O | O | O | H | F | H | H | CN | F | isobutyl | neopentyl |
| 53 | O | O | O | Br | H | H | H | H | H | mesityl | (nC₆H₁₃)₂CH– |
| 54 | O | O | O | NO₂ | H | H | H | H | H | cyclopropyl | cyclobutyl |
| 55 | O | O | O | CH₃ | nC₆H₁₃ | H | H | H | H | 4-Cl-benzyl | benzyl |
| 56 | O | O | O | CO₂CH₃ | H | H | H | H | H | 1-adamantyl | 2-adamantyl |
| 57 | O | O | O | H | –Ph | H | H | H | –Ph | cyclopentyl | cyclopentyl |
| 58 | O | O | O | —COOH | H | H | H | H | H | $C_2F_5$ | $CF_3$ |

-continued

| No. | | | | | | | | | | | |
|---|---|---|---|---|---|---|---|---|---|---|---|
| 59 | O | O | O | O | H | CF$_3$ | H | H | H | H | 2,6-diisopropyl-4-methylphenyl | 4-tert-butylphenyl |
| 60 | O | O | O | O | OCH$_3$ | H | H | H | H | H | -O-CH$_2$CH$_2$-* (ethoxy) | -CH$_2$CH$_2$CH$_2$CH$_2$-NH$_2$ |

Structure (perylene diimide-type core with labels R$^{N1}$, R$^{N2}$, X$^1$, X$^2$, X$^3$, X$^4$, R$^{22}$, R$^{23}$, R$^{25}$, R$^{26}$, R$^{27}$, R$^{28}$):

| No. | X$^1$ | X$^2$ | X$^3$ | X$^4$ | R$^{27}$ | R$^{22}$ | R$^{23}$ | R$^{28}$ | R$^{25}$ | R$^{26}$ | R$^{N1}$ | R$^{N2}$ |
|---|---|---|---|---|---|---|---|---|---|---|---|---|
| 61 | O | O | O | O | H | H | H | H | H | H | H | H |
| 62 | O | O | O | O | H | H | H | H | H | H | CH$_3$ | CH$_3$ |
| 63 | O | O | O | O | H | H | H | H | H | H | nC$_6$H$_{13}$ | nC$_6$H$_{13}$ |
| 64 | O | O | O | O | H | H | H | H | H | H | cyclohexyl | cyclohexyl |
| 65 | S | S | O | O | H | H | H | H | H | H | cyclohexyl | cyclohexyl |

-continued

| No. | | | | | | | | | | R | R' |
|---|---|---|---|---|---|---|---|---|---|---|---|
| 66 | O | O | S | S | H | H | H | H | H | cyclohexyl* | cyclohexyl* |
| 67 | O | S | S | S | H | H | H | H | H | cyclohexyl* | cyclohexyl* |
| 68 | O | O | O | O | H | H | H | H | H | CH$_2$C$_3$F$_2$ | CH$_2$C$_3$F$_2$ |
| 69 | O | O | O | O | H | H | H | H | H | -isoPropyl | -isoPropyl |
| 70 | O | O | O | O | H | H | H | H | H | -tert-Butyl | -tert-Butyl |
| 71 | S | S | O | O | H | H | H | H | H | C$_8$H$_{17}$-CH(C$_8$H$_{17}$)-* | C$_8$H$_{17}$-CH(C$_8$H$_{17}$)-* |
| 72 | O | O | O | O | H | H | H | H | H | C$_8$H$_{17}$-CH(C$_{10}$H$_{21}$)-* | C$_8$H$_{17}$-CH(C$_8$H$_{17}$)-* |
| 73 | O | O | O | O | H | H | H | H | H | C$_2$H$_4$C$_5$F$_{11}$ | C$_2$H$_4$C$_5$F$_{11}$ |
| 74 | O | O | O | O | Cl | Cl | Cl | Cl | Cl | cyclohexyl* | cyclohexyl* |
| 75 | O | O | O | O | F | F | H | H | H | phenyl* | phenyl* |
| 76 | O | O | O | O | F | F | F | F | F | mesityl* | mesityl* |
| 77 | O | O | O | O | CN | H | H | H | CN | neopentyl* | isobutyl* |

-continued

| # | | | | | | | | | | | | |
|---|---|---|---|---|---|---|---|---|---|---|---|---|
| 78 | O | O | O | O | Br | H | H | H | H | H | *-CH(nC₆H₁₃)(nC₈H₁₇) | mesityl |
| 79 | O | O | O | O | NO₂ | H | H | H | H | H | cyclobutyl* | cyclopropyl* |
| 80 | O | O | O | O | CH₃ | H | H | H | H | H | benzyl* | 4-Cl-benzyl* |
| 81 | O | O | O | O | CO₂CH₃ | nC₆H₁₃ | H | H | H | H | 1-adamantyl* | 1-adamantyl* |
| 82 | O | O | O | O | H | Ph | H | H | H | Ph | cyclopentyl* | cyclopentyl* |
| 83 | O | O | O | O | —COOH | H | H | H | H | H | CF₃ | C₂F₅ |

-continued

| No. | X¹ | X² | X³ | X⁴ | | | | | | |
|---|---|---|---|---|---|---|---|---|---|---|
| 84 | O | O | O | O | H | CF₃ | H | H | 2,6-diisopropyl-4-methylphenyl | 4-tert-butylphenyl |
| 85 | O | O | O | O | OCH₃ | H | H | H | ethoxyalkyl | aminobutyl |

Structure:

R^N1—N, R^N2—N, X¹, X², X³, X⁴, R²¹, R²², R²³, R²⁵, R²⁶, R²⁸ positions on fused polycyclic aromatic core with internal N atoms.

| No. | X¹ | X² | X³ | X⁴ | R²¹ | R²² | R²³ | R²⁸ | R²⁵ | R²⁶ | R^N1 | R^N2 |
|---|---|---|---|---|---|---|---|---|---|---|---|---|
| 86 | O | O | O | O | H | H | H | H | H | H | H | H |
| 87 | O | O | O | O | H | H | H | H | H | H | CH₃ | CH₃ |
| 88 | O | O | O | O | H | H | H | H | H | H | pent-4-en-1-yl | nC₆H₁₃ |
| 89 | O | O | O | O | H | H | H | H | H | H | cyclohexyl | cyclohexyl |
| 90 | S | S | O | O | H | H | H | H | H | H | nC₁₀H₂₁ | nC₁₀H₂₁ |

-continued

| No. | X¹ | X² | X³ | | | | | | | |
|---|---|---|---|---|---|---|---|---|---|---|
| 91 | O | O | S | H | H | H | H | cyclohexyl-* | cyclohexyl-* | |
| 92 | O | S | S | H | H | H | H | cyclohexyl-* | tetrahydropyran-2-yl-* | |
| 93 | O | S | O | thiophen-2-yl-* | H | H | H | acryloyloxybutyl-* | CH₂C₃F₇ | |
| 94 | O | O | O | H | thiazol-3-yl-* | furan-3-yl-* | H | -isoPropyl | -isoPropyl | |
| 95 | O | O | O | H | H | H | H | HO-(CH₂)ₙ-* | HO₃S-(CH₂)ₙ-* | |

| No. | X¹ | X² | X³ | X⁴ | R²¹ | R²² | R²³ | R²⁸ | R²⁵ | R²⁶ | Rᴺ¹ | Rᴺ² |
|---|---|---|---|---|---|---|---|---|---|---|---|---|
| 96 | O | O | O | O | H | H | H | H | H | H | H | H |
| 97 | O | O | O | O | H | H | H | H | H | H | CH₃ | CH₃ |
| 98 | O | O | O | O | H | H | H | H | H | H | pent-4-en-1-yl-* | nC₆H₁₃ |

-continued
| | | | | | | | | | | | | |
|---|---|---|---|---|---|---|---|---|---|---|---|---|
| 99 | O | O | O | O | H | H | H | H | H | H |  |  |
| 100 | S | O | S | O | H | H | H | H | H | H | nC$_{10}$H$_{21}$ | nC$_{10}$H$_{21}$ |
| 101 | O | S | O | O | H | H | H | H | H | H |  |  |
| 102 | O | S | S | S | H | H | H | H | H | H |  |  |
| 103 | O | O | O | O |  | H | H | H | H |  |  | CH$_2$C$_3$F$_7$ |
| 104 | O | O | O | O | H |  | H | H |  | H | -isoPropyl | -isoPropyl |
| 105 | O | O | O | O | H | H | H | H | H | H |  |  |

-continued

| No. | X¹ | X² | X³ | X⁴ | R²¹ | R²⁷ | R²⁴ | R²⁸ | R²⁵ | R²⁶ | R^{N1} | R^{N2} |
|---|---|---|---|---|---|---|---|---|---|---|---|---|
| 106 | O | O | O | O | H | H | H | H | H | H | H | H |
| 107 | O | O | O | O | H | H | H | H | H | H | CH₃ | CH₃ |
| 108 | O | O | O | O | Cl | H | H | H | H | H | nC₆H₁₃ | nC₆H₁₃ |
| 109 | O | O | O | O | F | H | H | H | H | H | cyclohexyl-CH₂-* | cyclohexyl-CH₂-* |
| 110 | S | S | S | O | H | H | H | H | H | H | cyclohexyl-CH₂-* | cyclohexyl-CH₂-* |
| 111 | O | O | S | S | CN | H | H | H | H | H | cyclohexyl-CH₂-* | cyclohexyl-CH₂-* |
| 112 | O | S | S | S | —N(CH₃)₂ | H | H | H | H | H | cyclohexyl-CH₂-* | cyclohexyl-CH₂-* |
| 113 | O | O | O | O | H | H | H | H | H | thienyl-* | CH₂C₃F₇ | CH₂C₃F₇ |

-continued

| # | | | | | | | | | | | | |
|---|---|---|---|---|---|---|---|---|---|---|---|---|
| 114 | O | O | O | O | H | [thiazol-3-yl] | H | H | [furan-3-yl] | H | -isoPropyl | -isoPropyl |
| 115 | O | O | O | O | H | H | H | H | H | H | $C_8H_{17}$/$C_8H_{17}$ (branched) | -tert-Butyl |
| 116 | S | S | S | S | H | H | H | H | H | H | $C_8H_{17}$/$C_{10}H_{21}$ (branched) | $C_8H_{17}$/$C_8H_{17}$ (branched) |
| 117 | O | O | O | O | H | H | H | H | H | H | $C_2C_4C_5F_{11}$ | $C_2H_4C_5F_{11}$ |
| 118 | O | O | O | O | H | H | H | H | H | H | cyclohexyl | cyclohexyl |
| 119 | O | O | O | O | Cl | H | Cl | H | H | H | phenyl | phenyl |
| 120 | O | O | O | O | F | H | F | F | F | F | mesityl | mesityl |
| 121 | O | O | O | O | F | H | F | F | F | F | neopentyl | isobutyl |
| 122 | O | O | O | O | CN | H | H | H | H | H | -$(CH_2)_7$-$P(O)(OH)_2$ | mesityl |
| 123 | O | O | O | O | Br | H | H | H | H | Br | — | — |

-continued

| # | | | | | | | | | | | |
|---|---|---|---|---|---|---|---|---|---|---|---|
| 124 | O | O | O | O | NO₂ | H | H | H | H | cyclobutyl | cyclopropyl |
| 125 | O | O | O | O | CH₃ | H | H | H | H | benzyl | 4-chlorobenzyl |
| 126 | O | O | O | O | CO₂CH₃ | H | H | H | H | adamantyl | adamantyl |
| 127 | O | O | O | O | H | H | H | H | H | cyclopentyl | cyclopentyl |
| 128 | O | O | O | O | —COOH | H | H | H | H | PhSi(CH₃)₂— | CF₃ |
| 129 | O | O | O | O | H | H | H | H | H | —≡—TIPS | C₂F₅ |
| 130 | O | O | O | O | OCH₃ | H | H | H | H | —(CH₂)ₙO—ethyl | —(CH₂)ₙNH₂ |

-continued

| No. | X¹ | X² | X³ | X⁴ | R²¹ | R²³ | R²⁴ | R²⁶ | R²⁵ | R²⁸ | R^{N1} | R^{N2} |
|---|---|---|---|---|---|---|---|---|---|---|---|---|
| 131 | O | O | O | O | H | H | H | H | H | H | H | H |
| 132 | O | O | O | O | CN | H | H | H | H | H | CH₃ | CH₃ |
| 133 | O | O | O | O | Br | H | H | H | H | Br | nC₆H₁₃ | nC₆H₁₃ |
| 134 | O | O | O | O | NO₂ | H | H | H | H | H | cyclohexyl | cyclohexyl |
| 135 | S | S | O | O | CH₃ | H | H | H | H | H | nC₁₃H₂₇ | nC₂₀H₄₁ |
| 136 | O | S | S | S | CO₂CH₃ | H | H | H | H | H | cyclohexyl | cyclohexyl |
| 137 | O | S | S | O | H | H | H | H | H | H | tetrahydropyranyl | tetrahydropyranyl |
| 138 | O | O | O | O | —COOH | H | H | H | H | H | —CH₂CH₂OCH₂CH₂OH | —CH₂CH₂OCH₂CH₂-(N-imidazolyl) |

-continued

| 139 | O | H | H | H | H | H | *~~~NH₂ | *~~~N(CH₃)₂ |
| 140 | O | OCH₃ | H | H | H | H | *~~~OH | *~~~SO₃H |

| No. | R²² | R²⁵ | R^N1 | R^N2 |
|---|---|---|---|---|
| 141 | H | H | 4-F-C₆H₄-* | 4-F-C₆H₄-* |
| 142 | H | H | CF₃ | CF₃ |
| 143 | H | H | nC₈H₁₇ | nC₈H₁₇ |
| 144 | H | H | nC₁₀H₂₁ | nC₁₀H₂₁ |
| 145 | H | H | 4-C₈H₁₇-C₆H₄-* | 4-C₈H₁₇-C₆H₄-* |
| 146 | H | H | 4-C₄H₉-C₆H₁₀-* | 4-C₄H₉-C₆H₁₀-* |

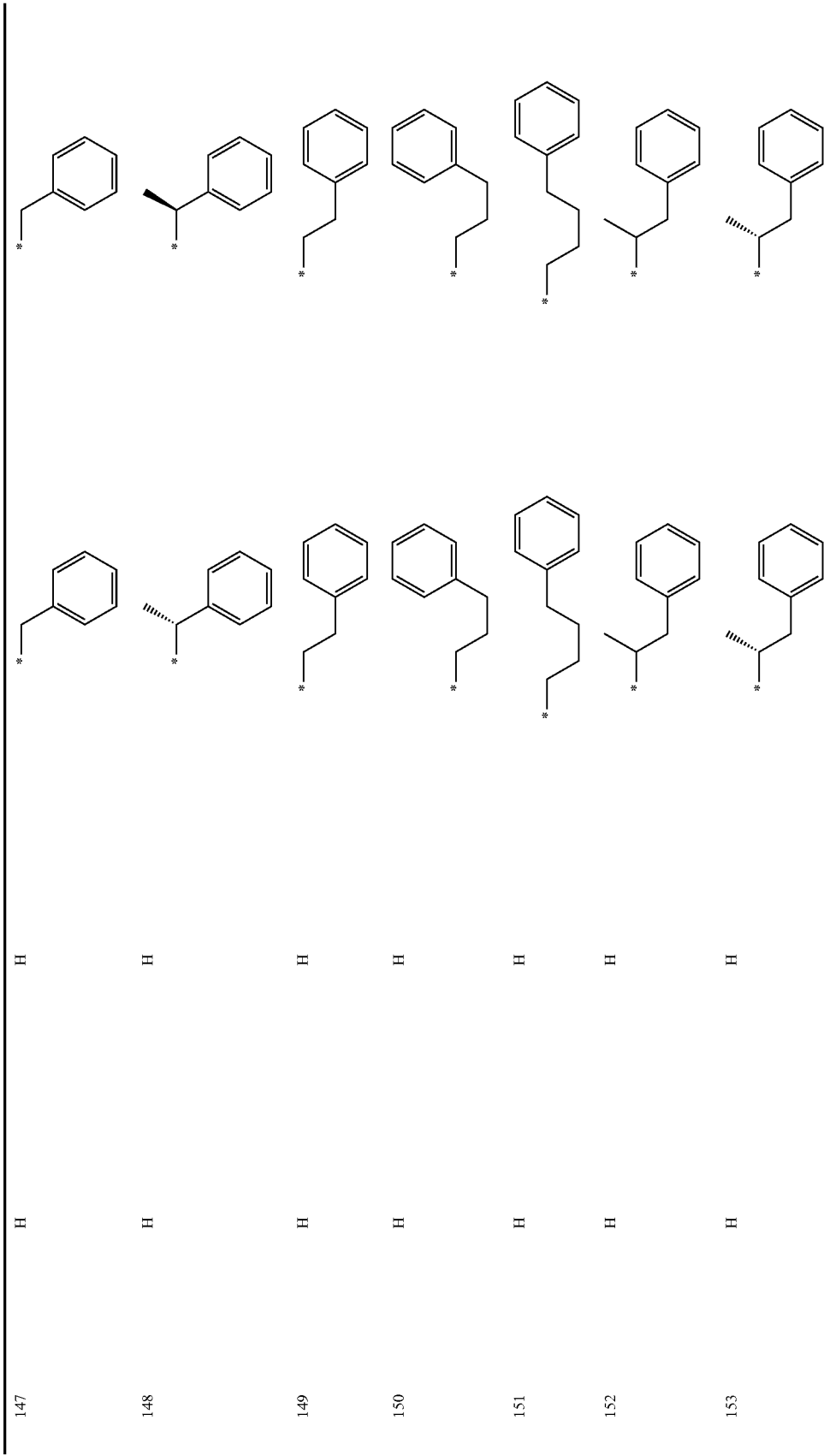

| | | | |
|---|---|---|---|
| 154 | H | H | pentafluorophenethyl / pentafluorophenethyl |
| 155 | H | H | 4-C8H17-tetrafluorophenethyl / 4-C8H17-tetrafluorophenethyl |
| 156 | H | H | 2-(pyridin-4-yl)ethyl / 2-(pyridin-4-yl)ethyl |
| 157 | H | H | 2-(pyridin-3-yl)ethyl / 2-(pyridin-3-yl)ethyl |
| 158 | H | H | 2-(pyrimidin-2-yl)ethyl / 2-(pyrimidin-2-yl)ethyl |
| 159 | H | H | 2-(1-C10H21-pyridinium-4-yl)ethyl I⁻ / same |
| 160 | H | H | 4-ethylphenethyl / 4-ethylphenethyl |
| 161 | H | H | 4-hexylphenethyl / 4-hexylphenethyl |
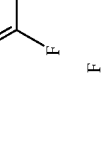

| | | |
|---|---|---|
| 162 | [structure: 4-C₁₀H₂₁-phenyl-ethyl] | [structure: 4-C₁₀H₂₁-phenyl-ethyl] |
| 163 | H | H |
| 164 | H | H |
| 165 | H | H |
| 166 | Br | Br |
| 167 | CN | CN |
| 168 | [2-thienyl] | [2-thienyl] |
| 169 | [2-selenophenyl] | [2-selenophenyl] |
| 170 | [2-furyl] | [2-furyl] |

-continued
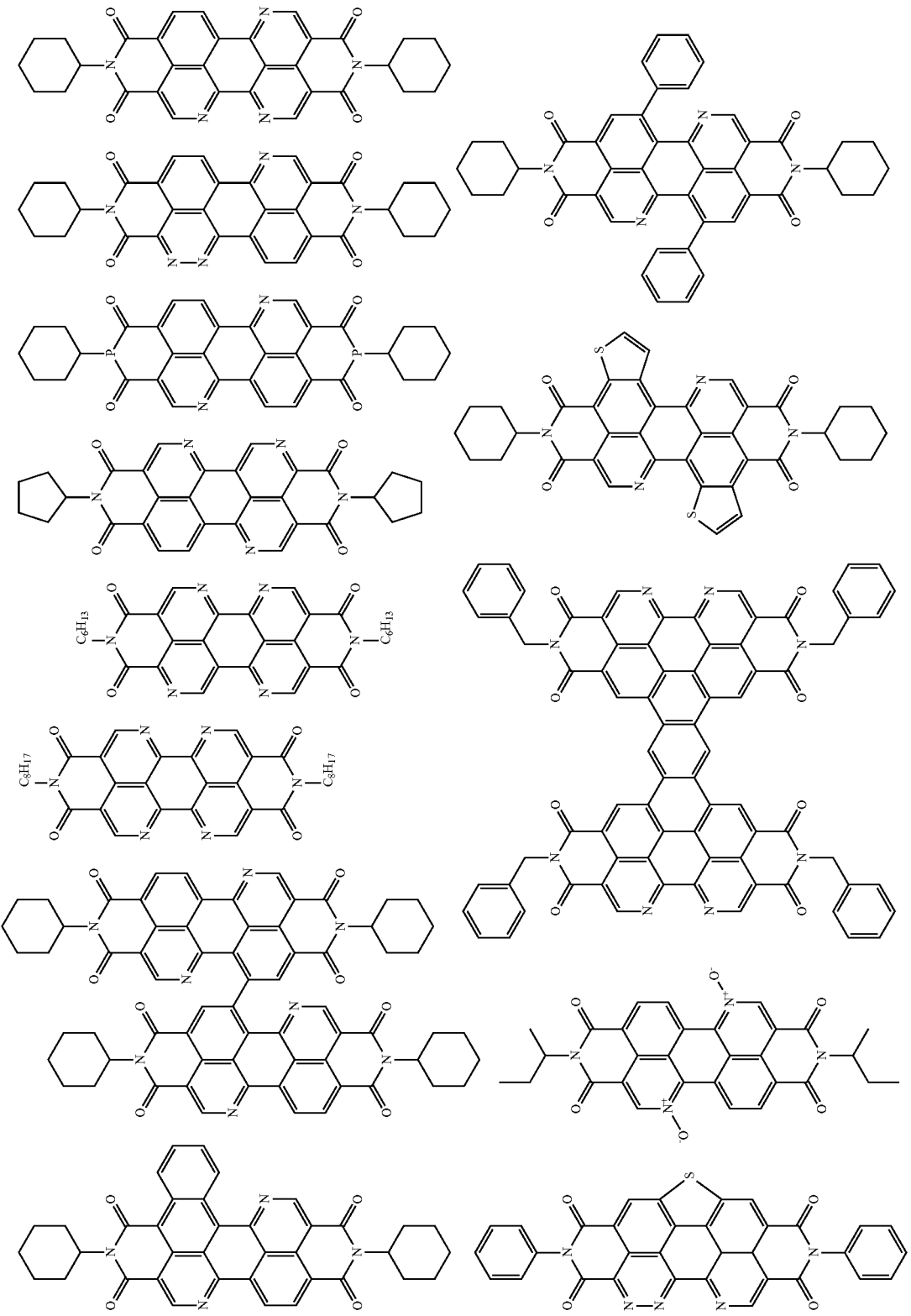

In the compound according to the embodiment of the present invention, from the viewpoints of improving carrier mobility and obtaining durability and further material stability, the molecular weight is preferably 350 or higher, more preferably 400 or higher, and still more preferably 500 or higher. In addition, from the viewpoint of solubility, the molecular weight is preferably 3000 or lower, more preferably 2000 or lower, and still more preferably 1000 or lower.

A synthesis method of the compound according to the embodiment of the present invention is not particularly limited, and the polymer according to the embodiment of the present invention can be synthesized using a typical method. For example, the synthesis method can refer to a synthesis method described in Chemical Communications, 2012, 48, p. 7961-7963 or a synthesis method described below in Examples.

[Organic Thin Film Transistor-Forming Composition]

Next, an organic thin film transistor-forming composition according to the embodiment of the present invention will be described.

This organic thin film transistor-forming composition (organic semiconductor film-forming composition) includes the compound according to the embodiment of the present invention, and is preferably used for forming an organic semiconductor film according to the embodiment of the present invention.

Compound According to Embodiment of Present Invention

As described above, as the compound according to the embodiment of the present invention, one kind may be used alone, or two or more kinds may be used in combination.

The content of the compound in the organic thin film transistor-forming composition is not particularly limited and can be expressed as, for example, the content in solid matter excluding the solvent described below. It is preferable that the content in the solid matter is in the same range as the content of the compound in the organic semiconductor film described below.

<Binder Polymer>

The organic thin film transistor-forming composition may include a binder polymer. In a case where the composition includes a binder polymer, an organic semiconductor film having a high film quality can be obtained.

The binder polymer is not particularly limited, and examples thereof include an insulating polymer such as polystyrene, poly(α-methylstyrene), polycarbonate, polyarylate, polyester, polyamide, polyimide, polyurethane, polysiloxane, polysulfone, polymethyl methacrylate, polymethyl acrylate, cellulose, polyethylene, or polypropylene and a copolymer thereof. Other examples of the binder polymer include a rubber such as an ethylene-propylene rubber, an acrylonitrile-butadiene rubber, a hydrogenated nitrile rubber, a fluororubber, a perfluoroelastomer, a tetrafluoroethylene-propylene copolymer, an ethylene-propylene-diene copolymer, a styrene-butadiene rubber, polychloroprene, polyneoprene, a butyl rubber, a methyl phenyl silicone resin, a methyl phenyl vinyl silicone resin, a methyl vinyl silicone resin, a fluorosilicone resin, an acrylic rubber, an ethylene acrylic rubber, chlorosulfonated polyethylene, chloropolyethylene, an epichlorohydrin copolymer, a polyisoprene-natural rubber copolymer, a polyisoprene rubber, a styrene-isoprene block copolymer, a polyester-urethane copolymer, a polyether-urethane copolymer, a polyether ester thermoplastic elastomer, or a polybutadiene rubber, and a thermoplastic elastomer polymer. Further, for example, a photoconductive polymer such as polyvinylcarbazole or polysilane, a conductive polymer such as polythiophene, polypyrrole, polyaniline, or polyparaphenylene vinylene, or a semiconductor polymer described in Chemistry of Materials, 2014, 26, 647 can also be used.

In consideration of charge mobility, it is preferable that the binder polymer has a structure not having a polar group. Here, the polar group refers to a functional group having a carbon atom and a heteroatom other than a hydrogen atom. As the binder polymer having a structure not having a polar group, polystyrene or poly(α-methylstyrene) is preferable. In addition, a semiconductor polymer is also preferable.

The glass transition temperature of the binder polymer is not particularly limited and is appropriately set according to the use or the like. For example, in a case where a strong mechanical strength is imparted to the organic semiconductor film, it is preferable to increase the glass transition temperature. On the other hand, in a case where flexibility is imparted to the organic semiconductor film, it is preferable to reduce the glass transition temperature.

As the binder polymer, one kind may be used alone, or two or more kinds may be used in combination.

The content of the binder polymer in the organic thin film transistor-forming composition is not particularly limited. For example, the content in the solid matter is preferably in the same range as the content of the binder polymer in the organic semiconductor film described below. In a case where an organic semiconductor film of an organic thin film transistor element is formed using the organic thin film transistor-forming composition in which the content of the binder polymer is in the above-described range, the carrier mobility and durability are further improved.

The weight-average molecular weight of the binder polymer is not particularly limited and is preferably 1000 to 10000000, more preferably 3000 to 5000000, and still more preferably 5000 to 3000000.

In the organic thin film transistor-forming composition, the compound according to the embodiment of the present invention may be uniformly mixed with the binder polymer, or a part or all of the compound according to the embodiment of the present invention may be phase-separated. From the viewpoints of coating easiness and coating uniformity, it is preferable that the compound according to the embodiment of the present invention and the binder polymer are uniformly mixed with each other at least during coating.

<Solvent>

The organic thin film transistor-forming composition may include a solvent. The solvent is not particularly limited as long as the above-described compound is soluble or dispersible therein, and examples thereof include an inorganic solvent and an organic solvent. Among these, an organic solvent is preferable. As the solvent, one kind may be used alone, or two or more kinds may be used in combination.

The organic solvent is not particularly limited, and examples thereof include: a hydrocarbon solvent such as hexane, octane, decane, toluene, xylene, mesitylene, ethylbenzene, amylbenzene, decaline, 1-methylnaphthalene, 1-ethylnaphthalene, 1,6-dimethylnaphthalene, or tetralin; a ketone solvent such as acetone, methyl ethyl ketone, methyl isobutyl ketone, cyclohexanone, acetophenone, propiophenone, or butyrophenone; a halogenated hydrocarbon solvent such as dichloromethane, chloroform, tetrachloromethane, dichloroethane, trichloroethane, tetrachloroethane, chlorobenzene, 1,2-dichlorobenzene, 1,2,4-trichlorobenzene, chlorotoluene, or 1-fluoronaphthalene; a heterocyclic compound such as pyridine, picoline, quinoline, thiophene, 3-butylthiophene, or thieno[2,3-b]thiophene; a halogenated heterocyclic solvent such as 2-chlorothiophene, 3-chlorothiophene, 2,5-dichlorothiophene, 3,4-dichlorothiophene, 2-bromothiophene, 3-bromothiophene, 2,3-dibromothiophene, 2,4-dibromothiophene, 2,5-dibromothiophene, 3,4-dibromothiophene, or 3,4-dichloro-1,2,5-thiadiazole; an ester solvent such as ethyl acetate, butyl acetate, amyl acetate, 2-ethylhexyl acetate, γ-butyrolactone, or phenyl acetate; an alcohol solvent such as methanol, propanol, butanol, pentanol, hexanol, cyclohexanol, methyl cellosolve, ethyl cellosolve, or ethylene glycol; an ether solvent such as dibutyl ether, tetrahydrofuran, dioxane, dimethoxyethane, anisole, ethoxybenzene, propoxybenzene, isopropoxybenzene, butoxybenzene, 2-methylanisole, 3-methylanisole, 4-methylanisole, 4-ethylanisole, dimethylanisole (any one of 2,3-, 2,4-, 2,5-, 2,6-, 3,4-, 3,5-, or 3,6-), or 1,4-benzodioxane; an amide solvent or an imide solvent such as N,N-dimethylformamide, N,N-dimethylacetamide, 1-methyl-2-pyrrolidone, 1-methyl-2-imidazolidinone, or 1,3-dimethyl-2-imidazolidinone; a sulfoxide solvent such as dimethyl sulfoxide; a phosphate solvent such as trimethyl phosphate; a nitrile solvent such as acetonitrile or benzonitrile; and a nitro solvent such as nitromethane or nitrobenzene.

Among these, a hydrocarbon solvent, a ketone solvent, a halogenated hydrocarbon solvent, a heterocyclic solvent, a halogenated heterocyclic solvent, or an ether solvent is preferable, toluene, xylene, mesitylene, amylbenzene, tetralin, acetophenone, propiophenone, butyrophenone, dichlorobenzene, anisole, ethoxybenzene, propoxybenzene, isopropoxybenzene, butoxybenzene, 2-methylanisole, 3-methylanisole, 4-methylanisole, 1-fluoronaphthalene, 3-chlorothiophene, or 2,5-dibromothiopheneis more preferable, and toluene, xylene, tetralin, acetophenone, propiophenone, butyrophenone, anisole, ethoxybenzene, propoxybenzene, butoxybenzene, 2-methylanisole, 3-methylanisole, 4-methylanisole, 1-fluoronaphthalene, 3-chlorothiophene, or 2,5-dibromothiophene is still more preferable.

In the organic thin film transistor-forming composition, among the above-described solvents, a solvent having a boiling point of 100° C. or higher is preferable from the viewpoints of improving film quality and increasing the grain size of crystals of the above-described compound.

Examples of the solvent having a boiling point of 100° C. or higher include toluene, xylene, mesitylene, tetralin, acetophenone, propiophenone, butyrophenone, dichlorobenzene, anisole, ethoxybenzene, propoxybenzene, isopropoxybenzene, butoxybenzene, 2-methylanisole, 3-methylanisole, and 4-methylanisole. Among these, toluene, xylene, tetralin, acetophenone, propiophenone, butyrophenone, anisole, ethoxybenzene, propoxybenzene, butoxybenzene, 2-methylanisole, 3-methylanisole, or 4-methylanisole, is more preferable.

In addition, it is still more preferable that the solvent having a boiling point of 100° C. or higher is a halogen-free solvent (solvent not having a halogen atom in a molecule) from the viewpoints of environmental burden and toxic effects on human.

The content of the solvent in the organic thin film transistor-forming composition is preferably 90 to 99.9 mass %, more preferably 95 to 99.9 mass %, and still more preferably 96 to 99.5 mass %.

<Other Components>

The organic thin film transistor-forming composition according to the embodiment of the present invention may further include components other than the compound according to the embodiment of the present invention and the solvent.

Examples of the components include various additives.

As the additives, any additives can be used without any particular limitation to additives which are typically used in an organic thin film transistor-forming composition. Examples of the additives include a surfactant, an antioxidant, a crystallization controller, and a crystal alignment controller. Examples of the surfactant and the antioxidant include those described in paragraphs "0136" and "0137" of JP2015-195362A, the content of which is incorporated herein by reference.

The content of the additives in the organic thin film transistor-forming composition is not particularly limited. For example, the content in the solid matter is preferably in the same range as the content of the additives in the organic semiconductor film described below. In a case where an organic semiconductor film of an organic thin film transistor is formed using the organic thin film transistor-forming composition in which the content of the additives is in the above-described range, film forming properties are excellent, the carrier mobility and heat resistance are further improved.

In the organic thin film transistor-forming composition according to the embodiment of the present invention, the viscosity is preferably 10 mPa·s or higher from the viewpoint of high water resistance.

Preparation Method

A preparation method of the organic thin film transistor-forming composition is not particularly limited, and a typical preparation method can be adopted. For example, the organic thin film transistor-forming composition according to the embodiment of the present invention can be prepared by appropriately stirring predetermined amounts of the respective components.

Optionally, the respective components may also be heated during or after the appropriate stirring. The heating temperature is not particularly and, for example, is determined to be in a range of 150° C. to 40° C. In a case where a solvent is used, the heating temperature is determined to be not only in the above-described range but also in a range lower than a boiling point of the solvent.

[Organic Thin Film Transistor]

Next, an organic thin film transistor (also referred to as "organic TFT") according to the embodiment of the present invention, which is a preferable aspect among the above-described organic semiconductor devices including the compound according to the embodiment of the present invention, will be described.

The organic TFT according to the embodiment of the present invention comprises an organic semiconductor film according to the embodiment of the present invention described below. As a result, in the organic TFT according to the embodiment of the present invention, high carrier mobility is exhibited, deterioration of the carrier mobility over time in the atmosphere is effectively suppressed, and thus stable driving can be realized.

In the embodiment of the present invention, an ambient temperature or humidity in the atmosphere is not particularly limited as long as it is a temperature or humidity in an usage environment of the organic thin film transistor. For example, the temperature is room temperature (20° C.), and the humidity is 10 to 90 RH %.

The organic TFT according to the embodiment of the present invention is preferably used as an organic field effect transistor (FET) and is more preferably used as an insulating gate type FET in which a gate and a channel are insulated from each other.

The thickness of the organic thin film transistor according to the embodiment of the present invention is not particularly limited. In a case where it is desired to reduce the thickness of the transistor, for example, the total thickness of the transistor is preferably 0.1 to 0.5 µm.

The organic TFT according to the embodiment of the present invention includes the organic semiconductor film according to the embodiment of the present invention (also referred to as "organic semiconductor layer" or "semiconductor active layer") and may further include a source electrode, a drain electrode, a gate electrode, and a gate insulating film.

The organic TFT according to the embodiment of the present invention includes, on a substrate, a gate electrode, an organic semiconductor film, a gate insulating film that is provided between the gate electrode and the organic semiconductor film, and a source electrode and a drain electrode that are provided adjacent to the organic semiconductor film and are linked to each other through the organic semiconductor film. In the organic TFT, the organic semiconductor film and the gate insulating film are provided adjacent to each other.

A structure of the organic thin film transistor according to the embodiment of the present invention is not particularly limited as long as it includes the respective layers. For example, any structure such as a bottom contact type (a bottom gate-bottom contact type and a top gate-bottom contact type) or a top contact type (a bottom gate-top contact type and a top gate-top contact type) may be adopted. It is more preferable that the organic thin film transistor according to the embodiment of the present invention is a bottom gate-bottom contact type or bottom gate-top contact type (collectively referred to as "bottom gate type").

Hereinafter, an example of the organic thin film transistor according to the embodiment of the present invention will be described with reference to the accompanying drawings.

—Bottom Gate-Bottom Contact Type Organic Thin Film Transistor—

FIG. 1 is schematic cross-sectional view showing a bottom gate-bottom contact type organic thin film transistor 10 that is an example of the organic thin film transistor according to an embodiment of the present invention.

As shown in FIG. 1, the organic thin film transistor 10 includes a substrate (base material) 1, a gate electrode 2, a gate insulating film 3, a source electrode 4A and a drain electrode 4B, an organic semiconductor film 5, and a sealing layer 6 in this order.

Hereinafter, the substrate (base material), the gate electrode, the gate insulating film, the source electrode, the drain electrode, the organic semiconductor film, and the sealing layer, and preparation methods thereof will be described in detail.

(Substrate)

The substrate functions to support the gate electrode, the source electrode, the drain electrode, and the like described below.

The kind of the substrate is not particularly limited, and examples thereof include a plastic substrate, a silicon substrate, a glass substrate, and a ceramic substrate. In particular, from the viewpoints of applicability to each device and costs, a glass substrate or a plastic substrate is preferable.

The thickness of the substrate is not particularly limited. The thickness of the substrate is, for example, preferably 10 mm or less, more preferably 2 mm or less, and still more preferably 1.5 mm or less. On the other hand, the thickness of the substrate is preferably 0.01 mm or more and more preferably 0.05 mm or more.

(Gate Electrode)

As the gate electrode, a typical electrode that is used as a gate electrode of an organic TFT can be used without any particular limitation.

A material (electrode material) which forms the gate electrode is not particularly limited, and examples thereof include: a metal such as gold, silver, aluminum, copper, chromium, nickel, cobalt, titanium, platinum, magnesium, calcium, barium, or sodium; a conductive oxide such as $InO_2$, $SnO_2$, or indium tin oxide (ITO); a conductive polymer such as polyaniline, polypyrrole, polythiophene, polyacetylene, or polydiacetylene; a semiconductor such as silicon, germanium, or gallium-arsenic; and a carbon material such as fullerene, carbon nanotube, or graphite. Among these, the metal is preferable, and silver or aluminum is more preferable.

The thickness of the gate electrode is not particularly limited and is preferably 20 to 200 nm.

The gate electrode may function as the substrate. In this case, the substrate is not necessarily provided.

A method of forming the gate electrode is not particularly limited, and examples thereof include a method of performing vacuum deposition (hereinafter, simply referred to as "deposition") or sputtering on the substrate using the above-described electrode material and a method of applying or printing an electrode-forming composition including the above-described electrode material. In addition, in a case where an electrode is patterned, examples of a patterning method include a printing method such as ink jet printing, screen printing, offset printing, or relief printing (flexographic printing); a photolithography method, and a mask deposition method.

(Gate Insulating Film)

The gate insulating film is not particularly limited as long as it is an insulating layer and may have a single-layer structure or a multi-layer structure.

A material which forms the gate insulating film is not particularly limited, and examples thereof include: a polymer such as polymethyl methacrylate, polystyrene, polyvinyl phenol, a melamine resin, polyimide, polycarbonate, polyester, polyvinyl alcohol, polyvinyl acetate, polyurethane, polysulfone, polybenzoxazole, polysilsesquioxane, an epoxy resin, or a phenolic resin; an inorganic oxide such as silicon dioxide, aluminum oxide, or titanium oxide; and a nitride such as silicon nitride. Among these, the above-described polymer is preferable from the viewpoint of affinity to the organic semiconductor film, and the above-described inorganic oxide, in particular, silicon dioxide is preferable from the viewpoint of the uniformity of the film.

As these materials, one kind may be used alone, or two or more kinds may be used in combination.

The thickness of the gate insulating film is not particularly limited and is preferably 100 to 1000 nm.

A method of forming the gate insulating film is not particularly limited, and examples thereof include: a method of applying a gate insulating film-forming composition including the above-described material to a substrate on which the gate electrode is formed; and a method of performing vacuum deposition or sputtering using the above-described material on the substrate on which the gate electrode is formed.

(Source Electrode and Drain Electrode)

In the organic TFT according to the embodiment of the present invention, the source electrode is an electrode into which a current flows from the outside through a wiring. In addition, the drain electrode is an electrode from which a current flows to the outside through a wiring.

As a material which forms the source electrode and the drain electrode, the same electrode material as that of the gate electrode can be used. Among these, a metal is preferable, and gold or silver is more preferable.

The thickness of each of the source electrode and the drain electrode is not particularly limited and is preferably 1 nm or more and more preferably 10 nm or more. The thickness is preferably 500 nm or less and more preferably 300 nm or less.

An interval (gate length) between the source electrode and the drain electrode can be appropriately determined and is, for example, preferably 200 µm or less and more preferably 100 µm or less. In addition, the gate width can be appropriately determined and is, for example, preferably 5000 µm or less and more preferably 1000 µm or less. Further, a ratio of a gate width W to a gate length L is not particularly limited. For example, the ratio W/L is preferably 10 or higher and more preferably 20 or higher.

A method of forming the source electrode and the drain electrode is not particularly limited, and examples thereof include a method of performing vacuum deposition or sputtering using the electrode material on the substrate on which the gate electrode and the gate insulating film are formed and a method of applying or printing an electrode-forming composition to or on the substrate. In a case where the source electrode and the drain electrode are patterned, a patterning method thereof is the same as that of the gate electrode.

(Organic Semiconductor Film)

The use of the organic semiconductor film according to the embodiment of the present invention is not particularly limited, and examples thereof include an organic semiconductor film included in each of the organic semiconductor devices. In particular, the organic semiconductor film according to the embodiment of the present invention is preferably used as an organic semiconductor film of the organic thin film transistor. Hereinafter, a case in which the organic semiconductor film according to the embodiment of the present invention is used as an organic semiconductor film of an organic thin film transistor will be described.

As the organic semiconductor film in the organic TFT according to the embodiment of the present invention, the organic semiconductor film according to the embodiment of the present invention including the compound according to the embodiment of the present invention is used. As the compound according to the embodiment of the present invention included in the organic semiconductor film, one kind may be used, or two or more kinds may be used.

In a case where the organic semiconductor film includes the compound according to the embodiment of the present invention, the carrier mobility is high, and the high carrier mobility can be maintained even after use or storage (left to standing) in the atmosphere. The reason for this is not clear but is presumed to be that, as described above, the compound according to the embodiment of the present invention exhibits low orbital energy of the lowest unoccupied molecular orbital.

The content of the compound according to the embodiment of the present invention in the organic semiconductor film is not particularly limited and can be appropriately set. For example, the content of the polymer is preferably 10 mass % or higher, more preferably 30 mass % or higher, and still more preferably 50 mass % or higher. The upper limit may be 100 mass %. In a case where the organic semiconductor film includes the binder polymer and the like, the upper limit is, for example, preferably 90 mass % or lower and more preferably 80 mass % or lower.

In addition to the compound according to the embodiment of the present invention, the organic semiconductor film may further include the above-described binder polymer. As the binder polymer, one kind may be included, or two or more kinds may be included.

A state where the organic semiconductor film includes the compound according to the embodiment of the present invention and the binder polymer is not particularly limited. However, from the viewpoint of carrier mobility, it is preferable that the compound according to the present invention and the binder polymer are phase-separated along a film thickness direction.

The content of the binder polymer in the organic semiconductor film is not particularly limited and can be appropriately set. For example, the content of the binder polymer is preferably 90 mass % or lower and more preferably 70 mass % or lower. The lower limit of the content may be 0 mass % or higher and, for example, is preferably 10 mass % or higher and more preferably 20 mass % or higher.

In addition to the compound according to the embodiment of the present invention, the organic semiconductor film may further include the above-described additives. As the additives, one kind may be included, or two or more kinds may be included.

The content of the additives in the organic semiconductor film is preferably 10 mass % or lower, more preferably 5 mass % or lower, and still more preferably 1 mass % or lower.

The thickness of the organic semiconductor film cannot be uniquely determined according to the organic thin film transistor to which the organic semiconductor film is applied and is, for example, preferably 10 to 500 nm and more preferably 20 to 200 nm.

The organic semiconductor film can be formed by applying the above-described organic thin film transistor-forming composition. The details will be described below.

(Sealing Layer)

As described above, the organic thin film transistor according to the embodiment of the present invention can be stably driven even in the atmosphere. Accordingly, it is not necessary to seal (block) the entire organic thin film transistor from the atmosphere (oxygen gas) water (it is not necessary to provide a sealing layer). Further, in order to realize stable driving for a long period of time, the entire organic thin film transistor can be sealed with a metallic sealing can or a sealing agent.

For the sealing layer, a sealing agent (sealing layer-forming composition) that is typically used in the organic TFT can be used. Examples of the sealing agent include an inorganic material such as glass or silicon nitride, a polymer material such as Parylene, and a low molecular weight material.

The sealing layer can be formed using the sealing agent with a typical method such as coating and drying.

The thickness of the sealing layer is not particularly limited and is preferably 0.2 to 10 µm.

—Bottom Gate-Top Contact Type Organic Thin Film Transistor—

Figure 2:
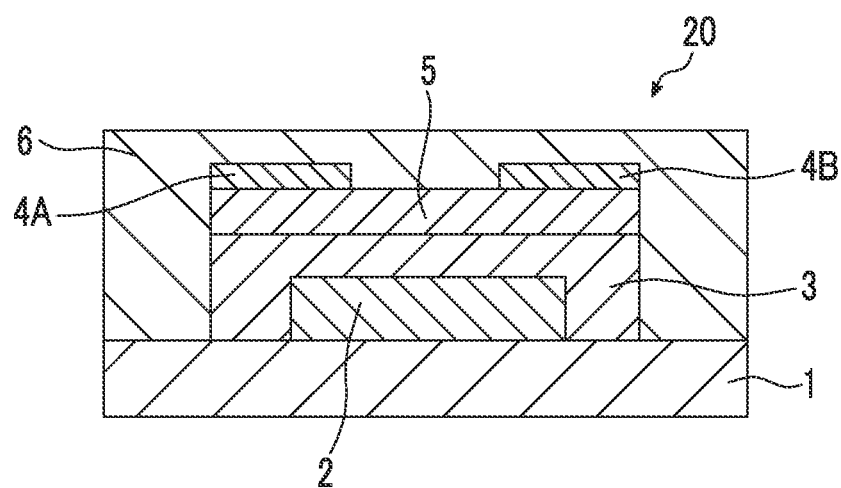
FIG. 2 is schematic cross-sectional view showing a bottom gate-top contact type organic thin film transistor that is an example of the organic thin film transistor according to the embodiment of the present invention.

FIG. 2 is a schematic cross-sectional view showing a bottom gate-top contact type organic thin film transistor 20 as an example of the semiconductor element according to the embodiment of the present invention.

As shown in FIG. 2, the organic thin film transistor 20 includes the substrate 1, the gate electrode 2, the gate insulating film 3, the organic semiconductor film 5, the source electrode 4A and the drain electrode 4B, and the sealing layer 6 in this order.

The organic thin film transistor 20 is the same as the organic thin film transistor 10 except for the layer configuration (stack aspect). Accordingly, the details of the substrate, the gate electrode, the gate insulating film, the source electrode, the drain electrode, the organic semiconductor film, and the sealing layer are the same as those of the bottom gate-bottom contact type organic thin film transistor, and thus the description thereof will not be repeated.

[Method of Manufacturing Organic Thin Film Transistor]

A method of manufacturing the organic thin film transistor according to the embodiment of the present invention is not particularly limited as long as it is a method including a step of forming an organic semiconductor film by applying the organic thin film transistor-forming composition according to the embodiment of the present invention to a substrate.

All of the gate electrode, the gate insulating film, the source electrode, the drain electrode, and the sealing layer can be prepared or formed using the above-described method.

Hereinafter, the step of forming the organic semiconductor film will be described.

In this step, the above-described organic thin film transistor-forming composition according to the embodiment of the present invention is used.

In the present invention, the application of the organic thin film transistor-forming composition to the substrate includes an aspect in which the organic thin film transistor-forming composition is directly applied to the substrate and an aspect in which the organic thin film transistor-forming composition is applied over the substrate through another layer provided on the substrate. The other layer (a layer that is provided adjacent to the organic semiconductor film and functions as a base of the organic semiconductor film) to which the organic thin film transistor-forming composition is applied is necessarily determined according to the structure of the organic thin film transistor. For example, in the case of a bottom gate type, the other layer is the gate insulating film, and in the case of a top gate type (a top gate-bottom contact type or a top gate-top contact type), the other layer is the source electrode or the drain electrode.

During the formation of the organic semiconductor film, the substrate may be heated or cooled. By changing the temperature of the substrate, the film quality or the packing of the compound according to the embodiment of the present invention in the film can be controlled.

The temperature of the substrate is not particularly limited. For example, the temperature of the substrate is set to be preferably in a range of 0° C. to 200° C., more preferably in a range of 15° C. to 100° C., and still more preferably 20° C. to 95° C.

The method of forming the organic semiconductor film is not particularly limited, and examples thereof include a vacuum process and a solution process both of which are preferable. In the present invention, the solution process is more preferable.

Examples of the vacuum process include a physical vapor deposition method such as a vacuum deposition method, a sputtering method, an ion plating method, or a molecular beam epitaxy (MBE) method, and a chemical vapor deposition (CVD) method such as plasma polymerization. Among these, a vacuum deposition method is preferable.

In the solution process, the organic thin film transistor-forming composition including the above-described solvent is preferably used.

As described above, the compound according to the embodiment of the present invention is stable in the atmosphere. Accordingly, the solution process can be performed in the atmosphere, and the organic thin film transistor-forming composition according to the embodiment of the present invention can be applied to a large area.

In the solution process, as a method of applying the organic thin film transistor-forming composition, a typical method can be used. Examples of the method include: a coating method such as a drop casting method, a cast method, a dip coating method, a die coater method, a roll coater method, a bar coater method, or a spin coating method; various printing methods such as an ink jet method, a screen printing method, a gravure printing method, a flexographic printing method, an off set printing method, or a microcontact printing method; and a method such as Langmuir-Blodgett (LB) method. Among these, a drop casting method, a cast method, a spin coating method, an ink jet method, a gravure printing method, a flexographic printing method, an off set printing method, or a microcontact printing method is preferable. In a preferable solution process described below, an ink jet method, a gravure printing method, a flexographic printing method, an off set printing method, or a microcontact printing method is preferable, and a flexographic printing method, a microcontact printing method or an ink jet method, is more preferable.

In the solution process, it is preferable that the organic thin film transistor-forming composition applied to the substrate is dried. It is more preferable that drying is slowly performed.

By drying the organic thin film transistor-forming composition, crystals of the compound according to the embodiment of the present invention can be precipitated, and the organic semiconductor film can be formed.

It is preferable that the organic thin film transistor-forming composition is dried on the heated substrate by performing natural drying or performing heating drying and then drying under reduced pressure from the viewpoint of film quality. The temperature of the substrate during natural drying or heating drying is preferably 20° C. to 100° C. and more preferably 50° C. to 80° C. The time of natural drying or heating drying is preferably 0.5 to 20 hours and more preferably 1 to 10 hours.

The temperature of the substrate during drying under reduced pressure is preferably 20° C. to 100° C. and more preferably 40° C. to 80° C. The time of drying under reduced pressure is preferably 1 to 20 hours and more preferably 2 to 10 hours. The pressure of drying under reduced pressure is preferably $10^{-6}$ to $10^{-2}$ Pa and more preferably $10^{-5}$ to $10^{-3}$ Pa.

For example, the dried organic thin film transistor-forming composition can be optionally shaped in a predetermined shape or pattern.

Hereinafter, a preferable solution process will be described with reference to the drawings.

In a method of forming the organic semiconductor film using the preferable solution process, the organic thin film transistor-forming composition according to the embodiment of the present invention (also referred to as "coating solution" in this process") is added dropwise (applied) to a part in a plane of the substrate so as to come into contact with a substrate and a member disposed on the substrate, and the added coating solution was dried. The substrate and the member used in the preferable solution process will be described below.

Here, regarding the substrate and the member disposed on the substrate, a state where the distance between the substrate and the member not adhering to the substrate is maintained at a given distance, or a state where the substrate and the member are in contact with each other is maintained.

As long as the above-described state is maintained, a positional relationship between the substrate and the member may be stationary or movable during the dropwise addition or drying of the coating solution. From the viewpoint of manufacturing efficiency, it is preferable that the positional relationship is movable. On the other hand, from the viewpoint of the film quality and crystal grain size of the obtained organic semiconductor film, it is preferable that the positional relationship is stationary.

In the preferable solution process, a method of adding the coating solution dropwise is not particularly limited. For example, during the dropwise addition of the coating solution, one droplet of the coating solution or two or more droplets of the coating solution may be added dropwise each time. It is preferable that one droplet is added dropwise each time from the viewpoint that a portion of the coating solution having a small thickness can be easily formed on the substrate and drying progresses from an end portion of the coating solution. In a case where the coating solution is added dropwise, the volume of one droplet of the coating solution is preferably 0.01 to 0.2 mL and more preferably 0.02 to 0.1 mL.

By adding the coating solution dropwise to a part in a plane of the substrate so as to come into contact with both the substrate and the member, the thickness in an end portion of the coating solution can be reduced.

A contact angle (25° C.) of the coating solution on the substrate is not particularly limited, and is preferably 0° to 90° and more preferably 10° to 20°. In a method of measuring the contact angle, an angle between a droplet and the substrate is measured one second after dropwise addition of the coating solution (solid content concentration: 0.1 mass %, solvent:anisole). Specifically, a static contact angle is measured with a drop method using a Teflon (registered trade name) probe under conditions of liquid amount: 1.0 µL or more. This way, the measurement is performed multiple times (typically, five times) on different substrates having undergone the above-described treatment, and the average value thereof is calculated as the contact angle.

It is preferable that the coating solution forms a meniscus on the member, and it is more preferable that the coating solution forms a concave meniscus from the viewpoint of film quality.

Figure 3:
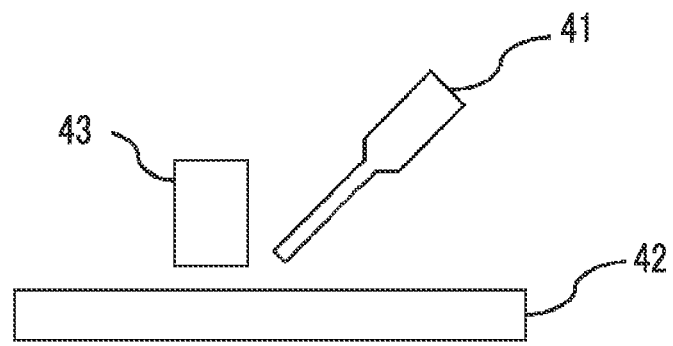
FIG. 3 is a schematic diagram showing a preferable method of forming an organic semiconductor film in a method of manufacturing the organic thin film transistor according to the embodiment of the present invention.
Figure 3:
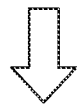
Figure 3:
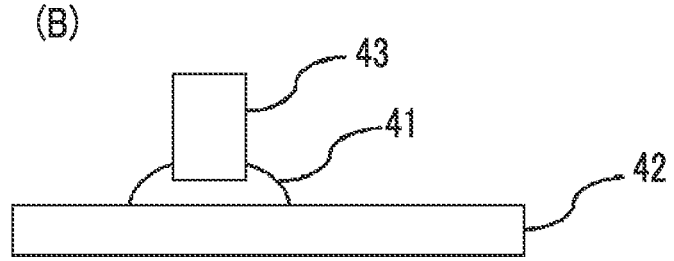
Figure 3:
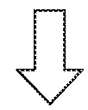
Figure 3:
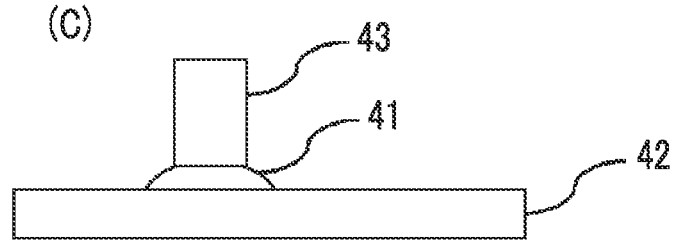

Examples of a method of applying the coating solution in a state where the distance between the substrate and the member is maintained at a given distance include a method shown in FIG. 3. In this method, first, a substrate 42 and a member 43 are disposed at predetermined positions. Specifically, the substrate 42 and the member 43 are disposed such that a state before adding the coating solution 41 dropwise to the substrate 1 is a state shown in (A) of FIG. 3. At this time, the distance between the substrate 42 and the member 43 not in contact with the substrate 42 is maintained at a given distance. The distance cannot be uniquely determined depending on the application amount, viscosity, and the like of the coating solution, and can be appropriately set.

Next, as shown in (B) of FIG. 3, the coating solution 41 is added dropwise to a part (in the vicinity of a portion where the substrate 42 and the member 43 face each other) of the substrate 42 so as to come into contact with both the substrate 42 and the member 43.

Next, in a state where a positional relationship between the substrate 42 and the member 43 is stationary (fixed), the coating solution 41 is dried preferably as described above. This state is shown in (C) of FIG. 3. The coating solution 41 is dried and crystallized in a direction from opposite end portions (edges) having a small thickness on the substrate 42 to the inside. As a result, the compound according to the embodiment of the present invention can be disposed at a predetermined position in the form of crystals having a large grain size.

After drying the coating solution 41, the member 43 is separated from the substrate 42. For example, the member 43 is vertically pulled up and separated from the substrate 42. As a result, an organic semiconductor film having a high film quality can be formed without forming a trace of the member 43 on the formed crystals.

This way, the organic semiconductor film formed of the crystals of the compound according to the embodiment of the present invention can be formed.

Figure 4:
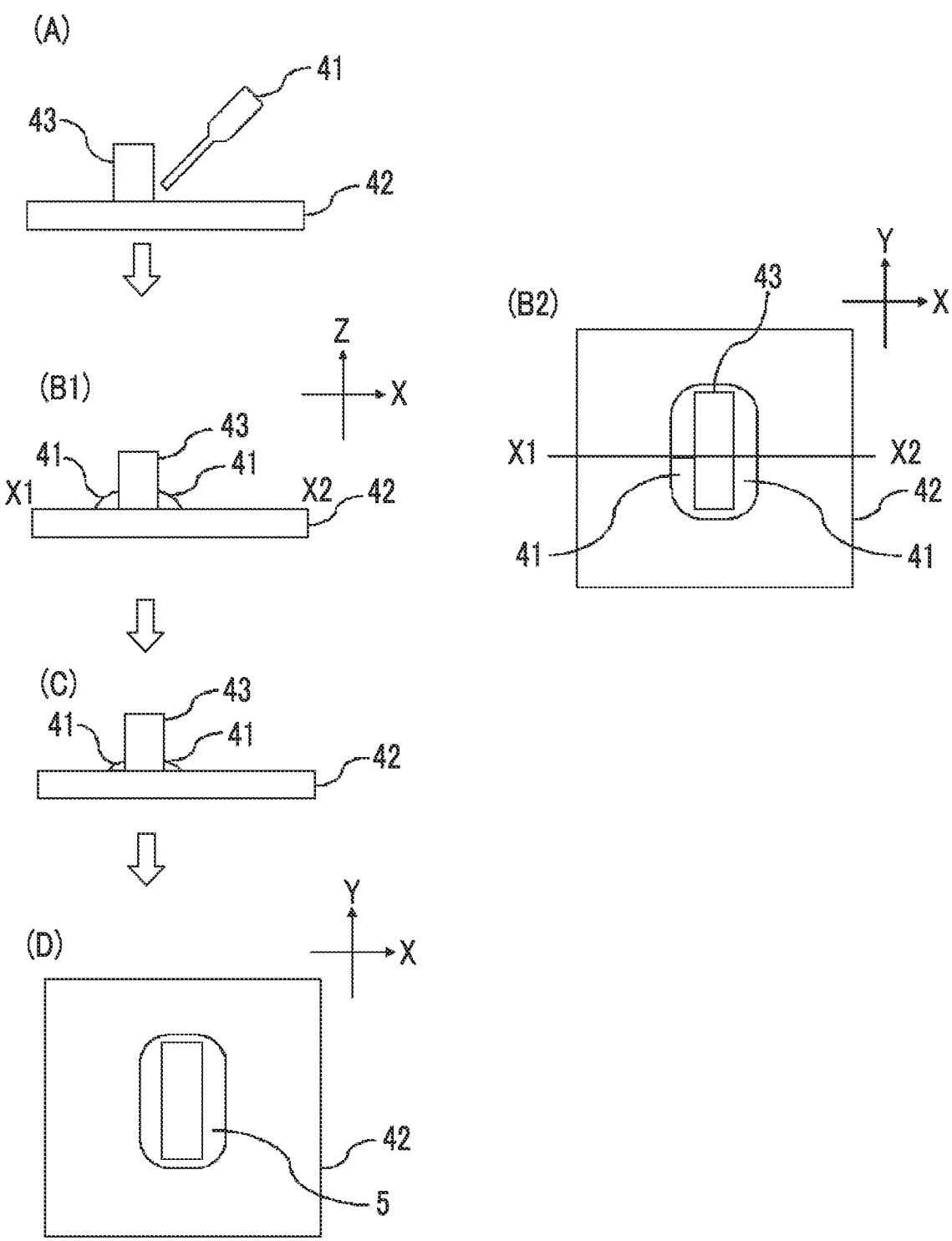
FIG. 4 is a schematic diagram showing the preferable method of forming the organic semiconductor film in the method of manufacturing the organic thin film transistor according to the embodiment of the present invention.

Examples of a method of applying the coating solution in a state where the substrate and the member are in contact with each other include a method shown in FIG. 4. In this method, first, the substrate 42 and the member 43 are disposed in contact with each other. Specifically, the member 43 is disposed on the substrate 42 such that a state before adding the coating solution 41 dropwise to the substrate 42 is a state shown in (A) of FIG. 4. Next, as shown in (B1) and (B2) of FIG. 4, the coating solution 41 is added dropwise to a part (in the vicinity of a contact portion where the substrate 42 and the member 43 are in contact with each other) of the substrate 42 so as to come into contact with both the substrate 42 and the member 43. At this time, it is preferable that the coating solution 41 surrounds the contact portion as shown in (B2) of FIG. 4. (B1) of FIG. 4 is a front view showing the substrate to which the coating solution is applied, and (B2) of FIG. 4 is a plan view showing the substrate to which the coating solution is applied. In (B1) and (B2) of FIG. 4, three-dimensional coordinates (X,Y,Z) are introduced.

Next, in a state where a positional relationship between the substrate 42 and the member 43 is stationary (fixed), the coating solution 41 is dried preferably as described above. This state is shown in (C) of FIG. 4. The coating solution 41 is dried and crystallized in a direction from opposite edges having a small thickness on the substrate 42 to the inside. As a result, the compound according to the embodiment of the present invention can be disposed at a predetermined position in the form of crystals having a large grain size.

After drying the coating solution 41, the member 43 is separated from the substrate 42, for example by vertically pulling up the member 43 from the substrate 42. As a result, as shown in (D) of FIG. 4, an organic semiconductor film 5 having a high film quality can be formed without forming a trace of the member 43 on the formed crystals.

This way, the organic semiconductor film formed of the crystals of the compound according to the embodiment of the present invention can be formed.

The method of applying the coating solution in a state where the substrate and the member are in contact with each other is preferable to the method of applying the coating solution in a state where the distance between the substrate and the member is maintained at a given distance from the viewpoints that the film quality is high, that a mechanism of holding the member 43 is unnecessary, and that the distance (contact state) from the member 43 to the substrate can be maintained.

Figure 5:
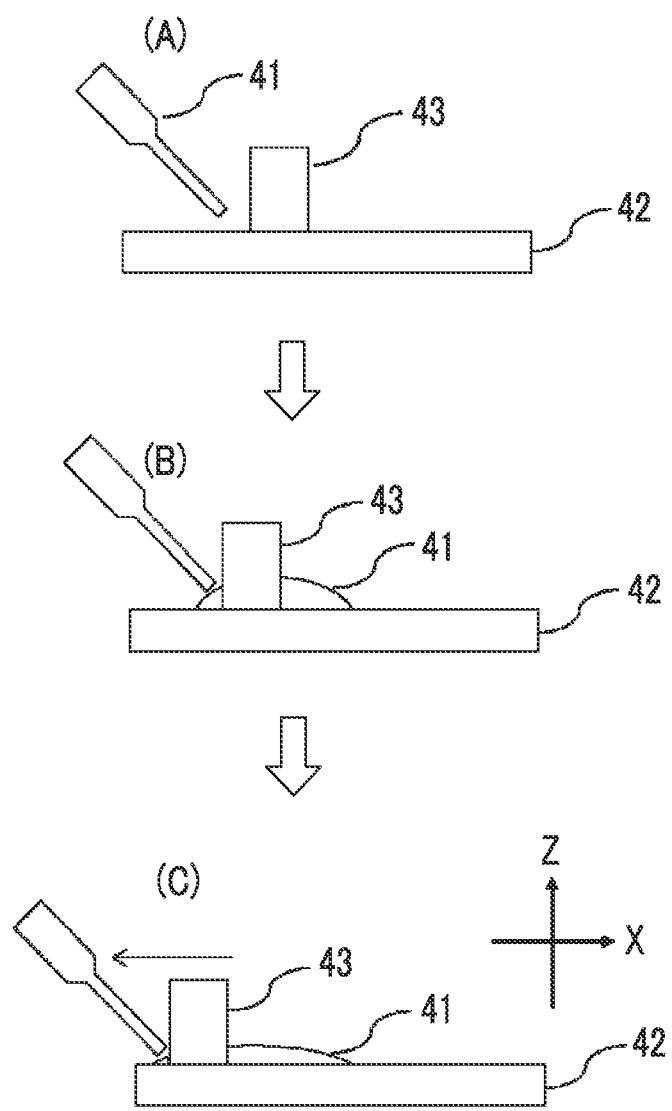
FIG. 5 is a schematic diagram showing the preferable method of forming the organic semiconductor film in the method of manufacturing the organic thin film transistor according to the embodiment of the present invention.

Examples of another method of applying the coating solution in a state where the substrate and the member are in contact with each other include a method shown in FIG. 5. This method is different from the method shown in FIG. 4 from the viewpoint of relatively moving the member 43 to promote the crystallization of the compound according to the embodiment of the present invention.

In this method shown in FIG. 5, first, the substrate 42 and the member 43 are disposed in contact with each other. Specifically, the member 43 is disposed on the substrate 42 such that a state before adding the coating solution 41 dropwise to the substrate 42 is a state shown in (A) of FIG. 5.

Next, as shown in (B) of FIG. 5, the coating solution 41 is added dropwise to a part (in the vicinity of a contact portion where the substrate 42 and the member 43 are in contact with each other) of the substrate 42 so as to come into contact with both the substrate 42 and the member 43. At this time, it is preferable that the coating solution 41 surrounds the contact portion as shown in (B2) of FIG. 4.

Next, the positional relationship between the substrate 42 and the member 43 is moved to dry the coating solution 41. For example, the member 43 is moved relative to the substrate 42 in a direction indicated by an arrow in the drawing (–X axis in (C) of FIG. 5). This state is shown in (C) of FIG. 5. The coating solution 41 is dried and crystallized from an end portion (X axis direction) opposite to a moving direction of the member 43 in the moving direction (–X axis direction). As a result, the compound according to the embodiment of the present invention can be disposed at a predetermined position in the form of crystals having a large grain size.

After drying the coating solution 41, the member 43 is separated from the substrate 42, for example by vertically pulling up the member 43 from the substrate 42. As a result, an organic semiconductor film having a high film quality can be formed without forming a trace of the member 43 on the formed crystals.

This way, the organic semiconductor film formed of the crystals of the compound according to the embodiment of the present invention can be formed.

The substrate used in the preferable solution process corresponds to the substrate of the organic thin film transistor, and is preferably the substrate on which the gate insulating film is formed.

The member 43 used in the preferable solution process is not particularly limited, and a material of the member 43 is preferably an inorganic material such as glass, quartz, or silicon or a plastic such as Teflon (registered trade name), polyethylene, or polypropylene, and more preferably glass.

Figure 6:
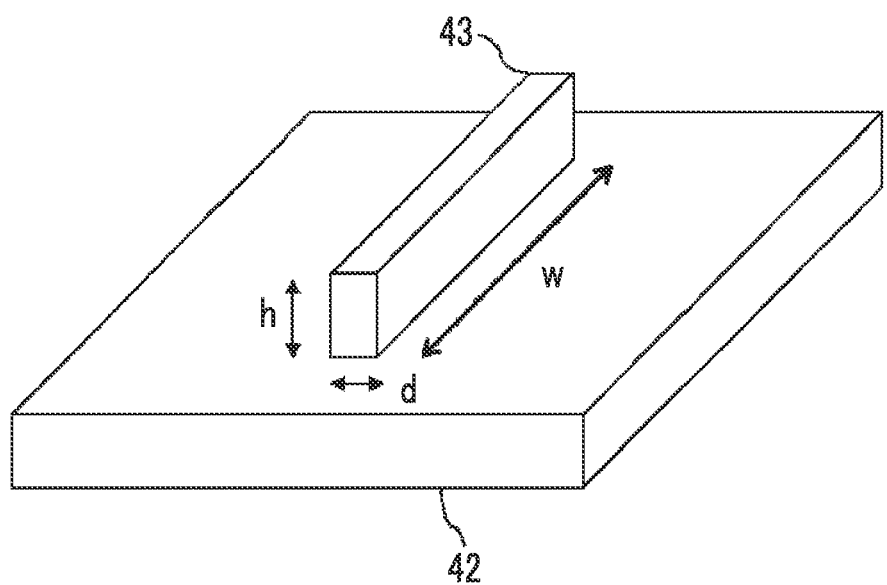
FIG. 6 is a schematic diagram showing an example of a substrate and members that are preferably used in the method of manufacturing the organic thin film transistor according to the embodiment of the present invention.

The size of the member 43 is not particularly limited. For example, regarding one side length (d or W in FIG. 6) of a surface of the member 43 facing the substrate 42, the lower limit value is preferably 0.1% or higher, more preferably 1% or higher, still more preferably 10% or higher, and even still more preferably 20% or higher with respect to one side length of the substrate 42. In addition, the upper limit value of the one side length is preferably 80% or lower, more preferably 70% or lower, and still more preferably 50% or lower with respect to one side length of the substrate 42. The height of the member 43 (h in FIG. 6) is preferably 1 to 50 mm and more preferably 5 to 20 mm. Further, a length ratio h/d of the member 43 is preferably 0.01 to 10 and, from the viewpoint of disposition stability of the member 43, more preferably 0.1 to 5. In addition, the length ratio W/d is preferably 1 to 1000 and, from the viewpoint that the compound according to the embodiment of the present invention can be crystallized in a wide range, more preferably 5 to 100.

This way, the organic semiconductor film according to the embodiment of the present invention can be formed by precipitating the crystals of the compound according to the embodiment of the present invention. Whether or not the crystals of the compound according to the embodiment of the present invention are precipitated can be determined by observing the organic semiconductor film using a polarizing microscope (trade name: Eclipse LV100N POL (transmitted/reflected illumination type), manufactured by Nikon Corporation, ocular lens: a magnification of 10-fold, objective lens: a magnification of 5 to 20-fold)

[Use of Organic Thin Film Transistor]

The use of the organic thin film transistor is not particularly limited, and the organic thin film transistor can be used as, for example, an electronic paper, a display device, a sensor, or an electronic tag.

EXAMPLES

The present invention will be described in more detail using Examples, but the present invention is not limited to the following Examples.

Synthesis Examples

Compounds 1 to 5 used in each of examples are shown below.

Each of the compounds was identified by $^1$H-NMR (400 MHz) in which tetramethylsilane was set as an internal standard. As a solvent, $CDCl_3$, dimethyl sulfoxide (DMSO)-d6, or tetrachloroethane-d2 was used.

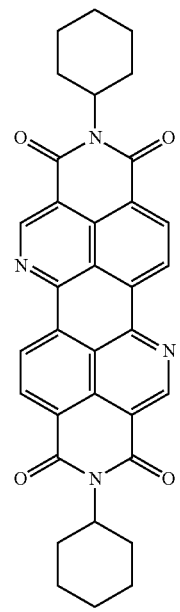

Compound 1

Compound 2

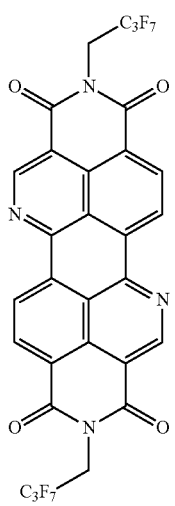

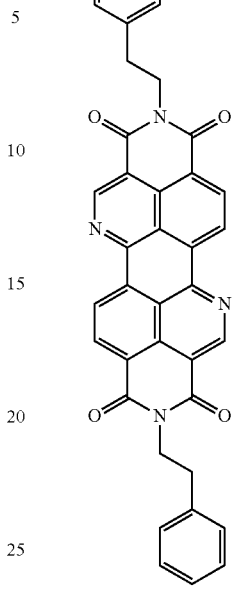

Compound 3

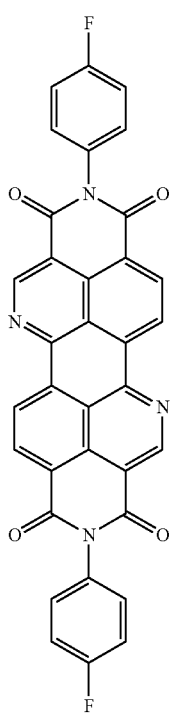

Compound 4

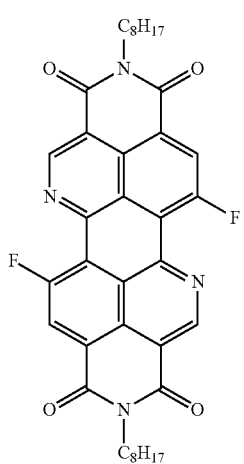

Compound 5

Synthesis Example 1: Synthesis of Compound 1

The compound 1 was synthesized according to the following scheme.

Synthesis of Compound 1-2: dimethyl-2,2'-(9,10-dioxo-9,10-dihydroanthracene-1,5-diyl) bis(2-cyanoacetate)

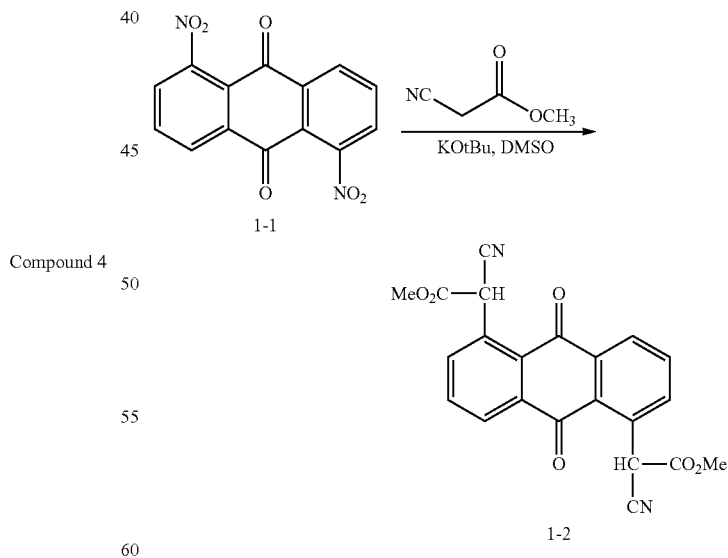

In the scheme, Me represents methyl, tBu represents t-butyl, and DMSO represents dimethyl sulfoxide.

At room temperature (20° C.), methyl cyanoacetate (133 g, 1.34 mol) was added to a dimethyl sulfoxide (600 mL) solution of 1,5-dinitroanthraquinone 1-1 (50 g, 168 mmol), and potassium-tert-butoxide (150.6 g, 1.34 mol) was further slowly added while paying attention to heat generation. The mixed solution was heated to 50° C. and was stirred for 3 hours. The reaction solution was cooled to room temperature and was poured into 2 L of iced water, and the reaction was stopped. Precipitates were separated by filtration and were purified by silica gel column chromatography (developing solvent=chlroform:ethyl acetate=98:2 (volume ratio)). As a result, a compound 1-2 (26.0 g, 64.6 mmol, yield: 38%) was obtained as a light orange solid.

$^1$H-NMR (CDCl$_3$) δ: 8.44 (dd, J=7.8, 1.3 Hz, 2H), 7.98 (brd, J=7.8 Hz, 2H), 7.90 (t, J=7.8, 2H), 6.02 (brs, 2H), 3.88 (s, 6H)

Synthesis of Compound 1-3: dimethyl-2,8-dihydroxybenzo[de]isoquinolino[1,8-gh]quinoline-3,9-dicarboxylate

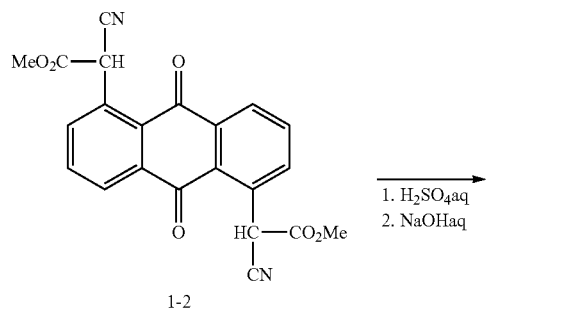

In the scheme, Me represents methyl.

A compound 1-2 (23.0 g, 57.2 mmol) was added to 230 mL of concentrated sulfuric acid, and the components were stirred for 30 minutes. The obtained concentrated sulfuric acid solution was poured into 1900 mL of water, was heated to 50° C., and was stirred for 20 minutes. 710 mL of a 50 w/v % sodium hydroxide aqueous solution was added dropwise to the obtained solution and was further heated and stirred at 80° C. for 10 minutes. The reaction solution was cooled to room temperature and then was neutralized with concentrated hydrochloric acid. Precipitates were separated by filtration and were cleaned with water and acetone. As a result, a compound 1-3 (20.0 g, 49.7 mmol, yield: 87%) was obtained as brown powder.

$^1$H-NMR (CDCl$_3$) δ: 8.97 (d, J=7.6 Hz, 2H), 8.88 (d, J=8.6 Hz, 2H), 7.87 (dd, J=8.6 Hz, 7.6 Hz, 2H), 4.18 (s, 6H)

Synthesis of Compound 1-4: dimethyl-2,8-bis(((trifluoromethyl)sulfonyl)oxy)benzo[de]isoquinolino[1,8-gh]quinoline-3,9-dicarboxylate

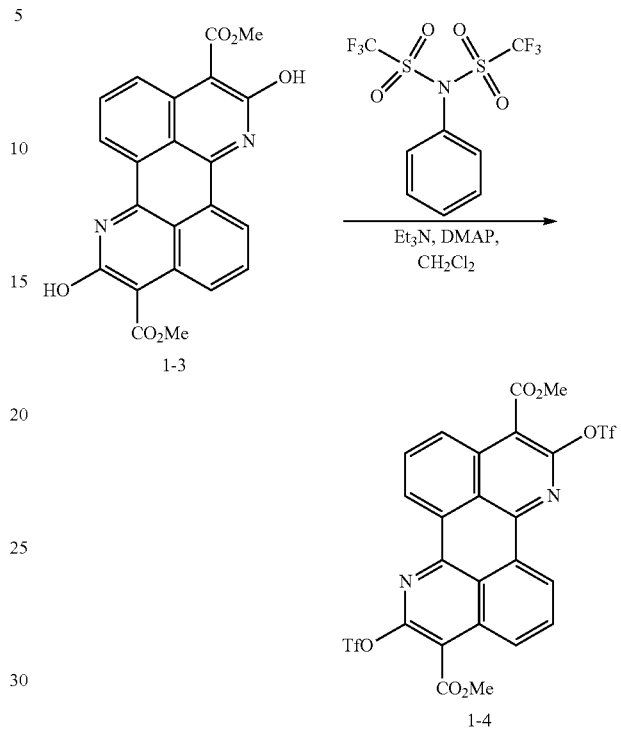

In the scheme, Me represents methyl, Et represents ethyl, DMAP represents 4-dimethylaminopyridine, and Tf represents trifluoromethanesulfonyl.

The compound 1-3 (17.0 g, 42.3 mmol), 4-dimethylaminopyridine (516 mg, 4.23 mmol), triethylamine (12.8 mL, 93.1 mmol), and 227 mL of dichloromethane were added to a reaction vessel and were cooled to −20° C. in an argon atmosphere. N-phenylbis(trifluoromethansulfonimide) (31.7 g, 88.8 mmol) was added to the reaction vessel, and the mixed solution was returned to room temperature and was stirred for 2 hours. The reaction solution was concentrated by drying under reduced pressure and was recrystallized from ethyl acetate. As a result, a compound 1-4 (20.0 g, 30.0 mmol, yield: 71%) was obtained as a yellow solid.

$^1$H-NMR (CDCl$_3$) δ: 8.97 (d, J=7.6 Hz, 2H), 8.88 (d, J=8.6 Hz, 2H), 8.93 (dd, J=8.6 Hz, 7.6 Hz, 2H), 4.18 (s, 6H)

Synthesis of Compound 1-5: dimethylbenzo[de]isoquinolino[1,8-gh]quinoline-3,9-dicarboxylate

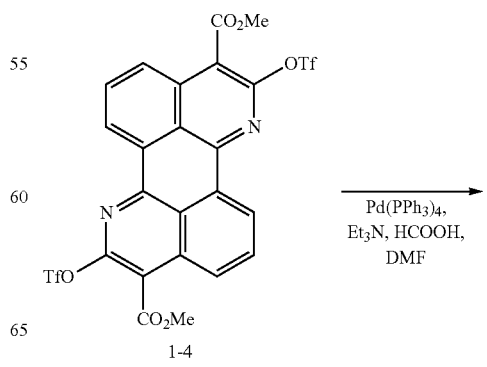

-continued

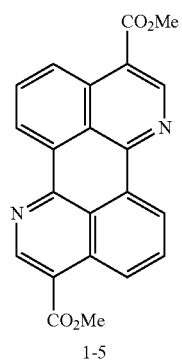

1-5

In the scheme, Me represents methyl, Et represents ethyl, Ph represents phenyl, Tf represents trifluoromethanesulfonyl, and DMF represents dimethylformamide.

The compound 1-4 (20.0 g, 30.0 mmol), tetrakis(triphenylphosphine)palladium (0) (3.47 g, 3.00 mmol), triethylamine (25.1 mL, 180 mmol), formic acid (6.79 mL, 180 mmol), and 250 mL of dimethylformamide were added to a reaction vessel, were heated to 80° C. in an argon atmosphere, and were stirred for 2 hours. The reaction solution was cooled to room temperature and was poured into 1 L of iced water, and the reaction was stopped. Precipitates were separated by filtration and were cleaned with water and acetone. As a result, a compound 1-5 (9.17 g, 24.8 mmol, yield: 83%) was obtained as a brown solid.

$^1$H-NMR (DMSO-d6) δ: 9.30 (s, 2H), 9.09 (m, 4H), 7.96 (dd, J=8.4 Hz, 7.6 Hz, 2H), 4.06 (s, 6H)

Synthesis of Compound 1-6: dimethyl-4,10-dibromobenzo[de]isoquinolino[1,8-gh]quinoline-3,9-dicarboxylate

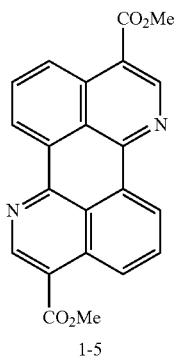 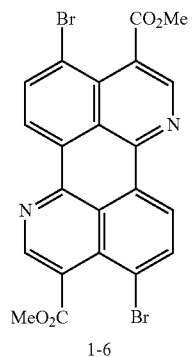

1-5        1-6

In the scheme, Me represents methyl, and NBS represents N-bromosuccinimide.

A 50 mL concentrated sulfuric acid solution of the compound 1-5 (4.00 g, 10.8 mmol) and N-bromosuccinimide (14.4 g, 81.0 mmol) were added to a reaction vessel, were heated to 50° C., and were stirred for 2.5 hours. Next, the reaction solution was poured into 500 mL of iced water, and the reaction was stopped. A 50 w/v % sodium hydroxide aqueous solution was added dropwise for neutralization. Next, precipitates were separated by filtration and were cleaned with water and acetone. As a result, a compound 1-6 (2.70 g, 5.11 mmol, yield: 47%) was obtained as a brown solid.

$^1$H-NMR (CDCl$_3$) δ: 8.90 (d, J=7.8 Hz, 2H), 8.72 (s, 2H), 8.18 (d, J=8.4 Hz, 2H), 4.04 (s, 6H)

Synthesis of Compound 1-7 3,9-dimethyl-4,10-bis(2,4,6-trichlorophenyl)benzo[de]isoquinolino[1,8-gh]quinoline-3,4,9,10-tetracarboxylate

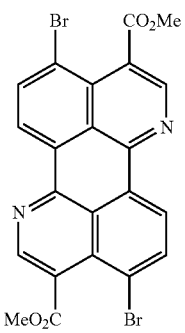 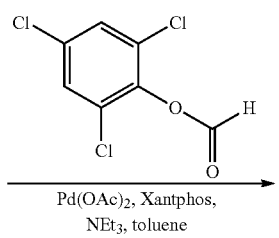

1-6

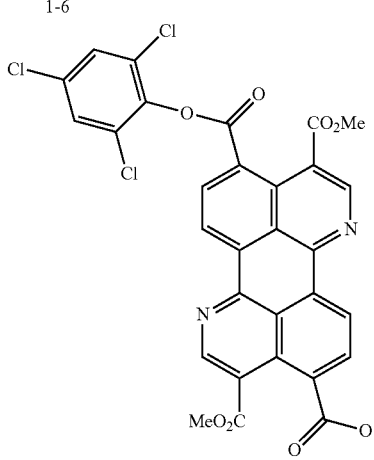

1-7

In the scheme, Me represents methyl, Et represents ethyl, Ac represents acetyl, Xantphos represents 4,5-bis(diphenylphosphino)-9,9-dimethylxanthene.

The compound 1-6 (1.40 g, 2.65 mmol), 2,4,6-trichlorophenyl formate (2.53 g, 10.6 mmol), palladium acetate (II) (59.5 mg, 0.265 mmol), 4,5-bis(diphenylphosphino)-9,9-dimethylxanthene (307 mg, 0.530 mmol), and 13.7 mL of toluene were added to a Schlenk flask, and deaeration and argon gas replacement were performed. In an argon atmosphere, triethylamine (1.47 mL, 10.6 mmol) was added to the obtained solution, was heated to 100° C., and was stirred for 12 hours. The reaction solution was cooled to room temperature, and then water was added. The organic layer was extracted with ethyl acetate, was cleaned with a saline solution, and was concentrated under reduced pressure. The concentration residue was purified by silica gel column chromatography (developing solvent: CHCl$_3$). As a result, a compound 1-7 (410 mg, 0.502 mmol, yield: 22%) was obtained as a light yellow solid.

$^1$H-NMR (CDCl$_3$) δ: 9.27 (d, J=8 Hz, 2H), 9.12 (s, 2H), 8.93 (d, J=8 Hz, 2H), 7.46 (s, 4H), 3.93 (s, 6H)

Synthesis of Compound 1-8

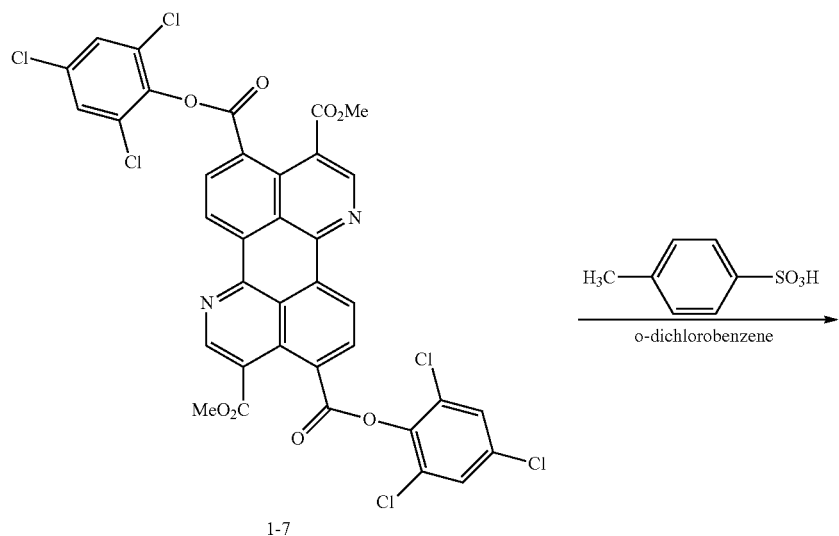

In the scheme, Me represents methyl.

The compound 1-7 (410 mg, 0.502 mmol), p-toluenesulfonic acid monohydrate (477 mg, 2.51 mmol), and 40 mL of o-dichlorobenzene were added to a reaction vessel, were heated to 120° C. in an argon atmosphere, and were stirred for 12 hours. Next, the reaction solution was dried under reduced pressure, and the solvent was removed by distillation. The solid content was dispersed in hexane, was separated by filtration, and was cleaned with hexane. As a result, a compound 1-8 (194 mg, 0.263 mmol, yield: 52%) was obtained.

$^1$H-NMR (CDCl$_3$) δ: 9.73 (s, 2H), 9.38 (d, J=7.6 Hz, 2H), 8.95 (d, J=7.6 Hz, 2H), 7.65 (d, J=7.8 Hz, 4H), 7.07 (d, J=7.6 Hz, 4H), 2.31 (s, 6H)

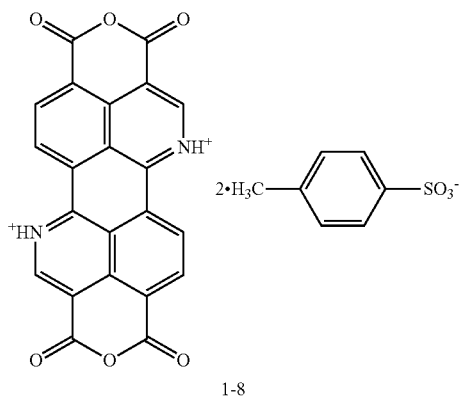

Synthesis of Compound 1

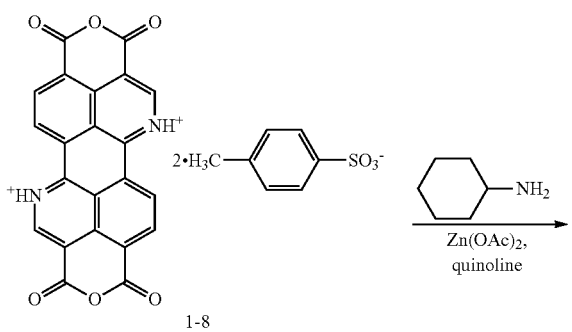

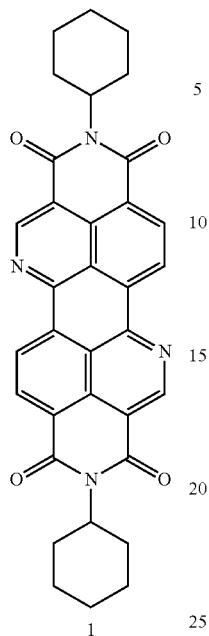

1

In the scheme, Ac represents acetyl.

The compound 1-8 (110 mg, 0.149 mmol), cyclohexylamine (5.8 μL, 0.328 mmol), anhydrous zinc (II) acetate (37.6 mg, 0.149 mmol), and 8.8 mL of quinoline were added to a reaction vessel, were heated to 120° C. in an argon atmosphere, and were stirred for 6 hours. Next, the reaction solvent was purified by silica gel column chromatography (developing solvent=chlroform:ethyl acetate=98:5 (volume ratio)) and was further purified by recrystallization (solvent=chloroform). As a result, a compound 1 (1.0 mg, 1.8 μmol, yield: 1.2%) was obtained as an orange solid.

$^1$H-NMR (tetrachloroethane-d2) δ: 9.61 (s, 2H), 9.24 (d, J=7.8 Hz, 2H), 8.81 (d, J=7.8 Hz, 2H), 5.00 (tt, J=12.4 Hz, 4 Hz, 2H), 2.52 (qd, J=12.4 Hz, 3.6 Hz, 4H), 1.91 (brd, J=13.6 HZ, 4H), 1.76 (brd, J=13.2 Hz, 6H), 1.50-1.23 (m, 6H)

Synthesis Example 2: Synthesis of Compound 2

According to the following scheme, a compound 2 was synthesized using the compound 1-8 obtained in Synthesis Example 1.

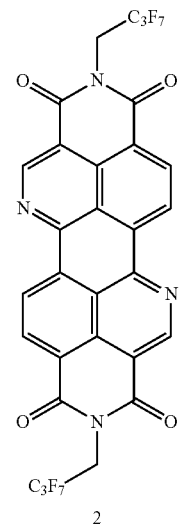

2

The compound 1-8 (150 mg, 0.203 mmol), 1H,1H-heptafluorobutylamine (108 μL, 0.812 mmol), 3 mL of propionic acid, and 9 mL of o-dichlorobenzene were added to a reaction vessel, were heated to 140° C. in an argon atmosphere, and were stirred for 6 hours. Under reduced pressure, the reaction solvent was removed by distillation, and the concentration residue was purified by silica gel column chromatography (developing solvent=tetrachloroethane:butyl acetate=90:10 (volume ratio)) and was further purified by recrystallization (solvent=tetrachloroethane). As a result, a compound 2 (97 mg, 0.128 mmol, yield: 63%) was obtained as an orange solid.

$^1$H-NMR (CDCl$_3$) δ: 9.71 (s, 2H), 9.35 (d, J=8 Hz, 2H), 8.92 (d, J=8 Hz, 2H), 5.00 (t, J=15.2 Hz, 4H)

Synthesis Example 3: Synthesis of Compound 3

According to the following scheme, a compound 3 was synthesized using the compound 1-8 obtained in Synthesis Example 1.

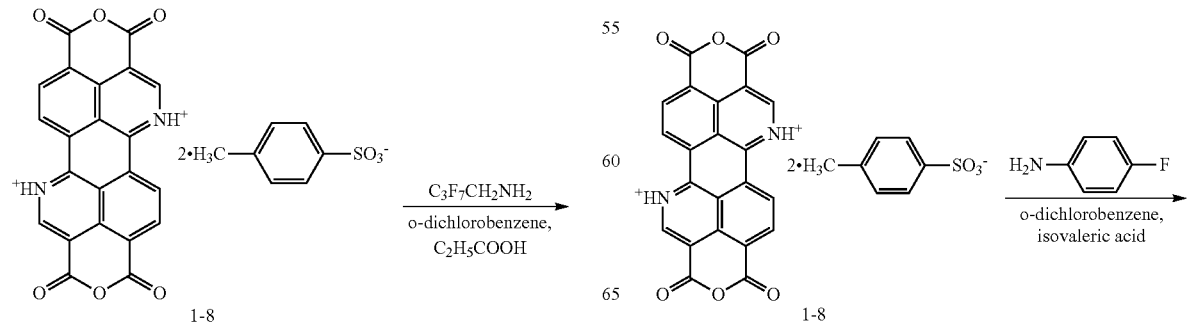

-continued

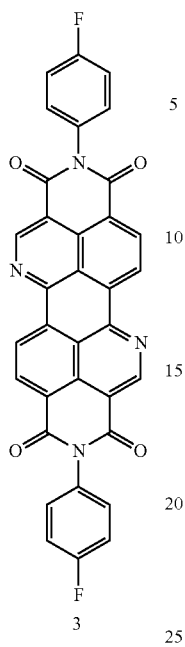

3

The compound 1-8 (30 mg, 0.0412 mmol), p-fluoroaniline (15.6 μL, 0.165 mmol), 0.6 mL of isovaleric acid, and 3 mL of o-dichlorobenzene were added to a reaction vessel, were heated to 140° C. in an argon atmosphere, and were stirred for 6 hours. Under reduced pressure, the reaction solvent was removed by distillation, and the concentration residue was purified by silica gel column chromatography (developing solvent=tetrachloroethane:butyl acetate=90:10 (volume ratio)) and was further purified by recrystallization (solvent:tetrachloroethane). As a result, a compound 3 (4.0 mg, 6.89 μmol, yield: 14%) was obtained as an orange solid.

$^1$H-NMR (tetrachloroethane-d2) δ: 9.73 (s, 2H), 9.39 (d, J=8 Hz, 2H), 8.92 (d, J=8 Hz, 2H), 7.39-7.26 (m, 8H)

Synthesis Example 4: Synthesis of Compound 4

According to the following scheme, a compound 4 was synthesized using the compound 1-8 obtained in Synthesis Example 1.

-continued

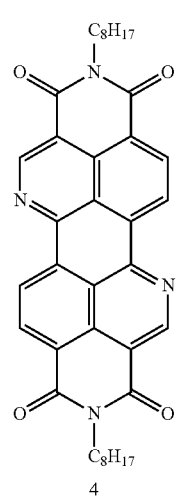

4

The compound 1-8 (100 mg, 0.135 mmol), n-octylamine (89.2 μL, 0.540 mmol), and 8 mL of propionic acid were added to a reaction vessel, were heated to 140° C. in an argon atmosphere, and were stirred for 6 hours. Under reduced pressure, the reaction solvent was removed by distillation, and the concentration residue was purified by silica gel column chromatography (developing solvent=chloroform:ethyl acetate=98:3 (volume ratio)) and was further purified by recrystallization (solvent=chloroform). As a result, a compound 4 (3.0 mg, 1.8 μmol, yield: 3.6%) was obtained as an orange solid.

$^1$H-NMR (tetrachloroethane-d2) δ: 9.64 (s, 2H), 9.28 (d, J=8 Hz, 2H), 8.84 (d, J=8 Hz, 2H), 4.16 (t, J=8 Hz, 4H), 1.73 (m, 4H), 1.44-1.20 (m, 20H), 0.87 (t, J=7.0 Hz, 6H)

Synthesis Example 5: Synthesis of Compound 5

Synthesis of Compound 1-9

First, according to the following scheme, a compound 1-9 was synthesized using the compound 1-8 obtained in Synthesis Example 1.

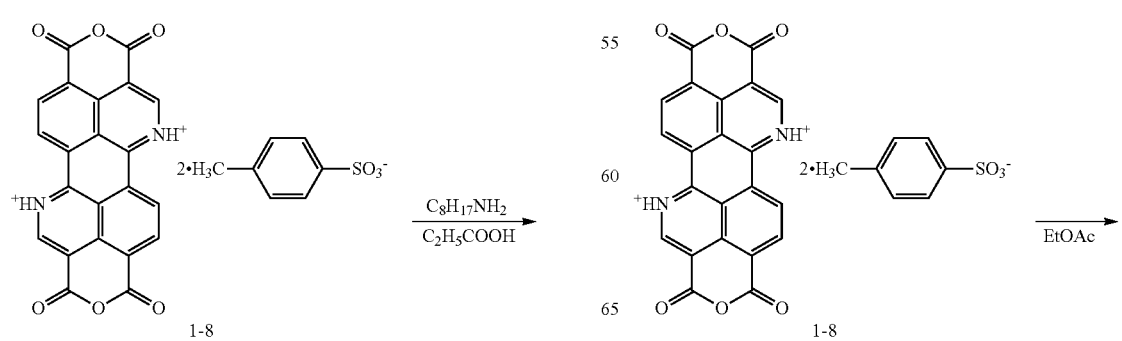

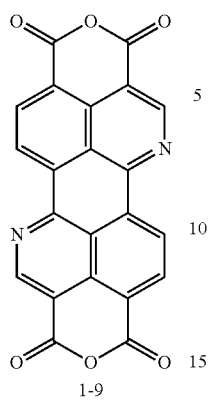

1-9

In the scheme, EtOAc represents ethyl acetate.

The compound 1-8 (194 mg, 0.263 mmol) was dispersed in ethyl acetate, was separated by filtration, and was cleaned with ethyl acetate. As a result, a compound 1-9 (95 mg, 0.240 mmol, yield: 91%) was obtained.

$^1$H-NMR (tetrachloroethane-d2) δ: 9.73 (s, 2H), 9.39 (d, J=8.0 Hz, 2H), 8.94 (d, J=8.0 Hz, 2H)

Synthesis of Compound 5

According to the following scheme, a compound 5 was synthesized using the compound 1-9.

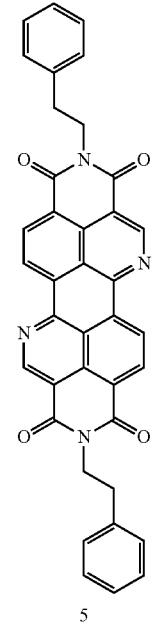

5

The compound 1-9 (494 mg, 1.25 mmol), phenylethylamine (350 µL, 2.77 mmol), 10 mL of propionic acid, and 40 mL of o-dichlorobenzene were added to a reaction vessel, were heated to 150° C. in an argon atmosphere, and were stirred for 15 hours. Next, methanol was added to the reaction solution, and precipitates were separated by filtration. The obtained crude purified product was purified by silica gel column chromatography (developing solvent: o-dichlorobenzene:ethyl acetate=98:2 (volume ratio)) and was further purified by recrystallization with tetrachloroethane. As a result, a compound 5 (88 mg, 0.15 µmol, yield: 12%) was obtained.

$^1$H-NMR (tetrachloroethane-d2) δ: 9.73 (s, 2H), 9.36 (d, J=7.2 Hz, 2H), 8.92 (d, J=7.2 Hz, 2H), 7.43-7.24 (m, 10H), 4.52 (t, J=8.0 Hz, 4H), 3.15 (t, J=8.0 Hz, 4H)

<Compounds for Comparison>

Comparative compounds c1 and c2 shown below were prepared.

The comparative compound c1 was synthesized with reference to the method described in WO2011/082234A.

The comparative compound c2 was synthesized with reference to the method described in Chemical Communications, 2012, 48, p. 7961-7963.

Comparative Compound c1

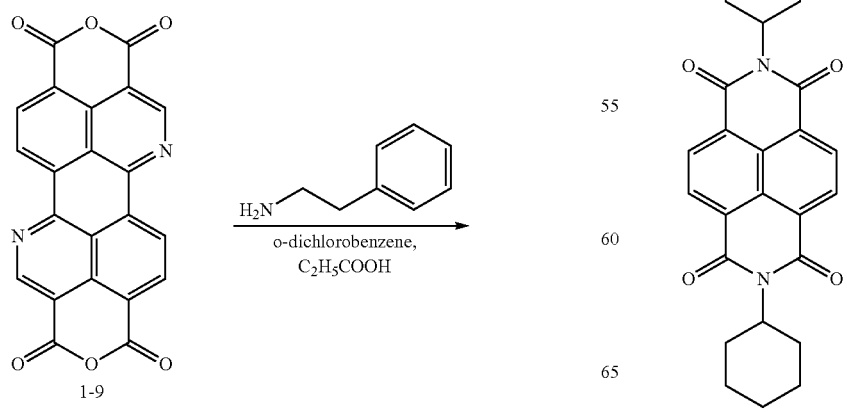

-continued

Comparative Compound c2

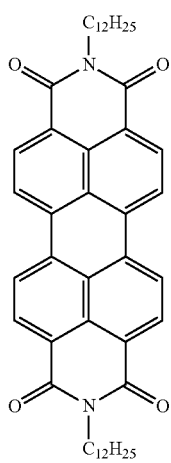

<Orbital Energy of Lowest Unoccupied Molecular Orbital>

The orbital energies of the lowest unoccupied molecular orbitals of the manufactured compounds 1 to 5 and the comparative compounds c1 and c2 were calculated as follows. The results are as shown below.

Compound 1: −4.17 eV
Compound 2: −4.18 eV
Compound 3: −4.18 eV
Compound 4: −4.17 eV
Compound 5: −4.17 eV
Comparative compound c1: −3.77 eV
Comparative compound c2: −3.81 eV Calculation method and conditions: the orbital energy of the lowest unoccupied molecular orbital was calculated using a density functional theory (DFT) method. Basic functions and functionals are as follows.

*B3LYP/6–31+G(d)//6–31G(d)*

Example 1

The bottom gate-top contact type organic thin film transistor 20 (in which the sealing layer 6 was not provided) having the structure shown in FIG. 2 was manufactured, and properties thereof were evaluated.

Preparation Example of Organic Thin Film Transistor-Forming Composition

The compound or comparative compound shown in Table 1 was dissolved in anisole as a solvent at a concentration of 0.1 mass %, and this reaction solution was heated to 50° C. This way, organic thin film transistor-forming compositions (solutions; also referred to as "compositions" in each of the tables) S1-1 to S1-5 and CS1-1 and CS1-2 were prepared.
<Manufacturing of Organic Thin Film Transistor>

As a substrate for measuring FET properties, a substrate (size: 25 mm×25 mm) in which a $SiO_2$ thermal oxide film (thickness: 200 nm) was formed on a surface of the n-type silicon substrate 1 (thickness: 0.4 mm; corresponding to the substrate 1 comprising the gate electrode 2) was prepared. A surface of the thermal oxide film (gate insulating film 3) of the substrate was cleaned with ultraviolet (UV)-ozone and then was treated with β-phenethyltrimethoxysilane.

A glass member having a size of 10 mm (length)×2 mm (width)×5 mm (height) was prepared. This member as the member 43 shown in FIG. 4 was disposed at a center portion of the β-phenethyltrimethoxysilane-treated surface of the substrate 1 in a state where the member was brought into contact with the treated surface as shown in (A) of FIG. 4.

Next, the substrate 1 (represented by reference numeral 42 in FIG. 4) was heated to 50° C., and as shown in (A) of FIG. 4, one droplet (about 0.05 mL) of each of the coating solutions S1-1 to S1-5 and CS1-1 and CS1-2 prepared using the above-described method was added dropwise using a pipette on the vicinity of a contact portion between the substrate 42 and the member 43 from a side portion of the member 43 so as to come into contact with the substrate 42 and the member 43. As shown in (B1) and (B2) of FIG. 4, the coating solution surrounded the contact portion and formed a concave meniscus at an interface with the member 43. A contact angle (25° C.) of the coating solution 41 on the substrate 42 was 10°.

As shown in (C) of FIG. 4, in a state where a positional relationship between the substrate 42 and the member 43 was stationary while maintaining the state where the substrate 42 and the member 43 were in contact with each other, the coating solution 41 was dried by natural drying or heating drying (temperature of substrate 42: 100° C., heating time: 8 hours). Next, by drying the coating solution 41 under a reduced pressure of $10^{-3}$ Pa at 60° C. for 8 hours, crystals of each of the compounds were precipitated. Next, the member 43 was vertically pulled up from the substrate 42 and separated from the substrate 42. As a result, the annular uniform organic semiconductor film 5 shown in (D) of FIG. 4 having the above-described thickness (thickness: 10 to 50 nm) was formed. The content of each of the compounds in the obtained organic semiconductor film 5 was 100 mass %.

The obtained organic semiconductor film 5 was observed using a polarizing microscope (trade name: Eclipse LV100N POL (transmitted/reflected illumination type), manufactured by Nikon Corporation, ocular lens: a magnification of 10-fold, objective lens: a magnification of 5 to 20-fold). As a result, it was verified that crystals of each of the compounds 1 to 5 were precipitated.

By disposing a mask having a predetermined opening on the obtained organic semiconductor film 5 and depositing gold, each of the source electrode 4A and the drain electrode 4B (thickness: 40 nm, gate width W=2 mm, gate length L=50 μm, ratio W/L=40) was formed. This way, each of organic thin film transistor (in each of the tables, also referred to as "OTFT") T1-1 to T1-5 for measuring FET properties and organic thin film transistors CT1-1 and CT1-2 for comparison was manufactured.
<Evaluation of Organic Thin Film Transistor>

Regarding each of the organic thin film transistors, the carrier mobility was evaluated under a normal atmospheric pressure of 1 atm (temperature: room temperature) using a semiconductor parameter analyzer (4156C, manufactured by Agilent Technologies Inc.) to which a semi-automatic prober (AX-2000, manufactured by Vector Semiconductor Co., Ltd.) was connected. The results are shown in Table 1.
(Evaluation of Carrier Mobility)
1. Measurement of Carrier Mobility $\mu^{ini}$ (Initial Carrier Mobility) after Manufacturing A voltage of −80 V was applied between the source electrode and the drain electrode of each of the organic thin film transistors, a gate voltage was caused to vary in a range of +20 V to −100 V, and a carrier mobility $\mu^{ini}$ (cm$^2$/Vs) was calculated using the following expression indicating a drain current $I_d$. An evaluation standard to which the calculated carrier mobility $\mu^{ini}$ belongs was determined among the following evaluation standards.

The higher the carrier mobility $\mu^{ini}$ the better. In this test, Rank C or higher is preferable, Rank B or higher is more preferable, and Rank A is still more preferable.

$$I_d = (w/2L)\mu C_i(V_g - V_{th})^2$$

In the expression, L represents the gate length, w represents the gate width, $\mu$ represents the carrier mobility, $C_i$ represents the volume of the gate insulating film per unit area, $V_g$ represents the gate voltage, and $V_{th}$ represents a threshold voltage.

—Evaluation Standards—

A: $1 \times 10^{-1}$ cm$^2$/Vs or higher

B: $1 \times 10^{-3}$ cm$^2$/Vs or higher and lower than $1 \times 10^{-1}$ cm$^2$/Vs C: $1 \times 10^{-4}$ cm$^2$/Vs or higher and lower than $1 \times 10^{-3}$ cm$^2$/Vs D: driving as a transistor was not realized (the current was not measured)

2. Measurement of Carrier Mobility $\mu^{af}$ after Standing in Atmosphere

Each of the manufactured organic thin film transistors was left to stand under a normal atmospheric pressure (temperature: room temperature, humidity: 50 RH %) for 1 week, and then the carrier mobility $\mu^{af}$ after standing was evaluated under the same conditions as those of "1. Measurement of Carrier Mobility $\mu^{ini}$ after Manufacturing".

TABLE 1

| OTFT No. | Composition No. | Compound No. | Carrier Mobility $\mu^{ini}$ | Carrier Mobility $\mu^{af}$ | Note |
|---|---|---|---|---|---|
| T1-1 | S1-1 | 1 | B | B | Present Invention |
| T1-2 | S1-2 | 2 | B | B | Present Invention |
| T1-3 | S1-3 | 3 | B | C | Present Invention |
| T1-4 | S1-4 | 4 | A | B | Present Invention |
| T1-5 | S1-5 | 5 | A | A | Present Invention |
| CT1-1 | CS1-1 | c1 | D | D | Comparative Example |
| CT1-2 | CS1-2 | c2 | C | D | Comparative Example |

The following can be seen from the results of Table 1.

In each of the organic thin film transistors CT1-1 and CT1-2, the carrier mobility $\mu^{af}$ after standing was not sufficient, and a function as an organic thin film transistor was not obtained.

That is, in the organic thin film transistor CT1-1, the initial carrier mobility μini was low, and a function as an organic thin film transistor was not obtained. In addition, in a case where the organic thin film transistor CT1-2 was left to stand in the atmosphere for 1 week, the carrier mobility decreased, and a function as an organic thin film transistor was not obtained.

On the other hand, each of the organic thin film transistors T1-1 to T1-5 according to the embodiment of the present invention comprises the organic semiconductor film including the compound according to the embodiment of the present invention. Therefore, the initial carrier mobility $\mu^{ini}$ was high, and the high carrier mobility $\mu^{af}$ was maintained even after standing in the atmosphere. This way, it was found that the organic thin film transistor according to the embodiment of the present invention has a high carrier mobility and can be stably driven for a long period of time in the atmosphere. In addition, the following was able to be verified. In each of the compounds 1 to 5 according to the embodiment of the present invention, the orbital energy of the lowest unoccupied molecular orbital (LUMO) was lower than −4.0 eV. In addition, although the use thereof is not particularly limited, the compound can be preferably used as an organic semiconductor material of an organic thin film transistor having the above-described excellent properties.

In particular, in a case where $A^{11}$ and $A^{12}$ in Formula (1) represent —N(R$^N$)— in which R$^N$ represents an alkyl group (compounds 1, 4, and 5) or an alkyl halide group (compound 2), both of the carrier mobilities $\mu^{ini}$ and $\mu^{af}$ were high (OTFTs No. T1-1, 2, 4, and 5).

Example 2

The bottom gate-bottom contact type organic thin film transistor 10 (in which the sealing layer 6 is not provided) having the structure shown in FIG. 1 was manufactured, and properties thereof were evaluated.

Preparation Example of Organic Thin Film Transistor-Forming Composition

The compound or comparative compound shown in Table 2 was dissolved in anisole as a solvent at a concentration of 0.1 mass %, and this reaction solution was heated to 100° C. This way, organic thin film transistor-forming compositions (solutions) S2-1 to S2-5 and CS2-1 and CS2-2 were prepared.

<Manufacturing of Organic Thin Film Transistor>

A substrate for measuring FET properties was prepared. In this substrate, a SiO$_2$ film (thickness: 200 nm) as the gate insulating film 3 was formed on the n-type silicon substrate 1 used in Example 1, and the source electrode 4A and the drain electrode 4B (thicknesses of the electrodes: 40 nm, gate width W=100 mm, gate length L=100 μm) were further formed and disposed on the gate insulating film 3 in a comb-like shape using chromium and gold.

Next, each of the organic thin film transistor-forming compositions S2-1 to S2-5 and CS2-1 and CS2-2 was cast on the substrate for measuring FET properties heated to 90° C. in a nitrogen atmosphere. As a result, the organic semiconductor film 5 was formed on the source electrode and the drain electrode. The content of each of the compounds in the obtained organic semiconductor film 5 was 100 mass %. In addition, the obtained organic semiconductor film 5 was observed using the polarizing microscope. As a result, it was verified that crystals of each of the compounds 1 to 5 were precipitated.

This way, each of organic thin film transistors T2-1 to T2-5 and organic thin film transistors CT2-1 and CT2-2 for comparison was manufactured.

<Evaluation of Organic Thin Film Transistor>

Regarding each of the manufactured organic thin film transistors, the carrier mobilities $\mu^{ini}$ and $\mu^{af}$ were evaluated under the same conditions as in Example 1. The results are shown in Table 2.

TABLE 2

| OTFT No. | Composition No. | Compound No. | Carrier Mobility $\mu^{ini}$ | Carrier Mobility $\mu^{af}$ | Note |
|---|---|---|---|---|---|
| T2-1 | S2-1 | 1 | B | C | Present Invention |

TABLE 2-continued

| OTFT No. | Composition No. | Compound No. | Carrier Mobility $\mu^{ini}$ | $\mu^{af}$ | Note |
|---|---|---|---|---|---|
| T2-2 | S2-2 | 2 | B | C | Present Invention |
| T2-3 | S2-3 | 3 | C | C | Present Invention |
| T2-4 | S2-4 | 4 | B | B | Present Invention |
| T2-5 | S2-5 | 5 | A | A | Present Invention |
| CT2-1 | CS2-1 | c1 | D | D | Comparative Example |
| CT2-2 | CS2-2 | c2 | D | D | Comparative Example |

The following can be seen from the results of Table 2.

In each of the organic thin film transistors CT2-1 and CT2-2, both of the carrier mobilities $\mu^{ini}$ and $\mu^{af}$ were not sufficient, and a function as an organic thin film transistor was not obtained.

On the other hand, each of the organic thin film transistors T2-1 to T2-5 according to the embodiment of the present invention was a bottom gate-bottom contact type in which the area of a surface of the organic semiconductor film exposed to the atmosphere was large, but the organic semiconductor film thereof included the compound according to the embodiment of the present invention. Therefore, the initial carrier mobility $\mu^{ini}$ was high, and the high carrier mobility $\mu^{af}$ was maintained even after standing in the atmosphere. This way, the organic thin film transistor according to the embodiment of the present invention had a high carrier mobility and was able to be stably driven for a long period of time in the atmosphere. In addition, the compound 1-5 according to the embodiment of the present invention can be preferably used as an organic semiconductor material of the organic thin film transistor having the above-described excellent properties.

In particular, in a case where $A^{11}$ and $A^{12}$ in Formula (1) represent —N($R^N$)— in which $R^N$ represents an alkyl group or an alkyl halide group (compounds 1, 2, 4, and 5), both of the carrier mobilities $\mu^{ini}$ and $\mu^{af}$ were high.

Example 3

The bottom gate-bottom contact type organic thin film transistor 10 (in which the sealing layer 6 is not provided) having the structure shown in FIG. 1 was manufactured, and properties thereof were evaluated.

Preparation Example of Organic Thin Film Transistor-Forming Composition

The compound or comparative compound shown in Table 3 and poly(α-methylstyrene) (mass ratio=1:1) were dissolved in anisole as a solvent at a total concentration of 0.1 mass %. Next, this reaction solution was heated to 100° C. This way, organic thin film transistor-forming compositions (solutions; also referred to as "compositions" in each of the tables) S3-1 to S3-5 and CS3-1 and CS3-2 were prepared.

The weight-average molecular weight of poly(α-methylstyrene) was 20000.

<Manufacturing of Organic Thin Film Transistor>

Each of organic thin film transistors T3-1 to T3-5 and organic thin film transistors CT3-1 and CT3-2 for comparison was manufactured under the same conditions as in Example 2, except that the organic thin film transistor-forming compositions S3-1 to S3-5 and CS3-1 and CS3-2 were used instead of the organic thin film transistor-forming compositions S2-1 to S2-5 and CS2-1 and CS2-2 during the manufacturing of the organic thin film transistor according to Example 2.

In the organic semiconductor film of each of the organic thin film transistors, the content of the compound according to the embodiment of the present invention and poly(α-methylstyrene) was 50 mass %. The obtained organic semiconductor film was observed using the polarizing microscope. As a result, it was verified that crystals of each of the compounds 1 to 5 were precipitated.

<Evaluation of Organic Thin Film Transistor>

Regarding each of the manufactured organic thin film transistors, the carrier mobilities $\mu^{ini}$ and $\mu^{af}$ were evaluated under the same conditions as in Example 1. The results are shown in Table 3.

TABLE 3

| OTFT No. | Composition No. | Compound No. | Carrier Mobility $\mu^{ini}$ | $\mu^{af}$ | Note |
|---|---|---|---|---|---|
| T3-1 | S3-1 | 1 | B | C | Present Invention |
| T3-2 | S3-2 | 2 | B | C | Present Invention |
| T3-3 | S3-3 | 3 | C | C | Present Invention |
| T3-4 | S3-4 | 4 | B | B | Present Invention |
| T3-5 | S3-5 | 5 | A | B | Present Invention |
| CT3-1 | CS3-1 | c1 | D | D | Comparative Example |
| CT3-2 | CS2-2 | c2 | D | D | Comparative Example |

The following can be seen from the results of Table 3.

In each of the organic thin film transistors CT3-1 and CT3-2, both of the carrier mobilities $\mu^{ini}$ and $\mu^{af}$ were not sufficient, and a function as an organic thin film transistor was not obtained.

On the other hand, each of the organic thin film transistors T3-1 to T3-5 according to the embodiment of the present invention was a bottom gate-bottom contact type, but the organic semiconductor film thereof included the compound according to the embodiment of the present invention and the binder polymer. Therefore, the initial carrier mobility $\mu^{ini}$ was high, and the high carrier mobility $\mu^{af}$ was maintained even after standing in the atmosphere. This way, the organic thin film transistor according to the embodiment of the present invention had a high carrier mobility and was able to be stably driven for a long period of time in the atmosphere. In addition, the compound 1-5 according to the embodiment of the present invention can be preferably used as an organic semiconductor material of the organic thin film transistor having the above-described excellent properties.

Further, it was verified that, regarding $A^{11}$ and $A^{12}$ in Formula (1), the same tendency as in Example 2 was exhibited.

The present invention has been described using the embodiments. However, unless specified otherwise, any of the details of the above description is not intended to limit the present invention and can be construed in a broad sense within a range not departing from the concept and scope of the present invention disclosed in the accompanying claims.

The present application claims priority based on JP2016-126449 filed on Jun. 27, 2016 and JP2017-122786 filed on Jun. 23, 2017, the entire contents of which are incorporated herein by reference.

EXPLANATION OF REFERENCES

1: substrate
2: gate electrode
3: gate insulating film
4A: source electrode
4B: drain electrode
5: organic semiconductor film
6: sealing layer
10, 20: organic thin film transistor
41: coating solution
42: substrate
43: member

What is claimed is:

1. A compound represented by the following Formula (2),

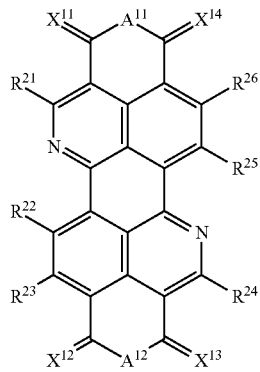

(2)

in Formula (2), $A^{11}$ and $A^{12}$ each independently represent —O—, —N($R^N$)—, or —P($R^N$)—, $R^N$ represents a hydrogen atom or an unsubstituted alkyl group; an alkyl group substituted with a halogen atom or a phenyl group, an unsubstituted phenyl group, a phenyl group substituted with a halogen atom, or a phenyl group having an alkyl group substituted with a halogen atom, $R^{21}$ to $R^{26}$ each represent a hydrogen atom, and $X^{11}$ to $X^{14}$ each independently represent an oxygen atom or a sulfur atom.

2. The compound according to claim 1, wherein all of $X^{11}$ to $X^{14}$ represent an oxygen atom.

3. The compound according to claim 1, wherein both $A^{11}$ and $A^{12}$ represent —N($R^N$)—, and $R^N$ represents a hydrogen atom or an unsubstituted alkyl group; an alkyl group substituted with a halogen atom or a phenyl group, an unsubstituted phenyl group, a phenyl group substituted with a halogen atom, or a phenyl group having an alkyl group substituted with a halogen atom.

4. The compound according to claim 1, wherein $R^N$ represents an unsubstituted alkyl group having 1 to 20 carbon atoms, an alkyl group substituted with a halogen atom or a phenyl group; an unsubstituted phenyl group, or a phenyl group substituted with a halogen atom.

* * * * *